US006429199B1

(12) United States Patent
Krieg et al.

(10) Patent No.: US 6,429,199 B1
(45) Date of Patent: Aug. 6, 2002

(54) IMMUNOSTIMULATORY NUCLEIC ACID MOLECULES FOR ACTIVATING DENDRITIC CELLS

(75) Inventors: Arthur M. Krieg, Iowa City, IA (US); Gunther Hartmann, München (DE)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 09/191,170

(22) Filed: Nov. 13, 1998

Related U.S. Application Data

(63) Continuation-in-part of application No. 08/960,774, filed on Oct. 30, 1997, now Pat. No. 6,239,116, which is a continuation-in-part of application No. 08/738,652, filed on Oct. 30, 1996, now Pat. No. 6,207,646, which is a continuation-in-part of application No. 08/386,063, filed on Feb. 7, 1995, now Pat. No. 6,194,388, which is a continuation-in-part of application No. 08/276,358, filed on Jul. 15, 1994, now abandoned.

(51) Int. Cl.[7] .................................................. A61P 37/04

(52) U.S. Cl. ....................................................... 514/44

(58) Field of Search ........................................... 514/44

(56) References Cited

U.S. PATENT DOCUMENTS

| | | | |
|---|---|---|---|
| 3,906,092 A | 9/1975 | Hilleman et al. | 424/209.1 |
| 4,469,863 A | 9/1984 | Ts'o et al. | 536/24.5 |
| 5,023,243 A | 6/1991 | Tullis | 514/44 |
| 5,248,670 A | 9/1993 | Draper et al. | 514/44 |
| 5,569,585 A | 10/1996 | Goodwin et al. | 435/6 |
| 5,585,479 A | 12/1996 | Hoke et al. | 536/24.5 |
| 5,663,153 A | 9/1997 | Hutcherson et al. | 514/44 |
| 5,723,335 A | 3/1998 | Hutcherson et al. | 435/375 |
| 5,738,852 A | 4/1998 | Robinson et al. | 424/199.1 |
| 5,766,920 A | 6/1998 | Babbitt et al. | 435/240.1 |
| 5,786,189 A | 7/1998 | Locht et al. | 435/172.3 |
| 5,849,719 A | 12/1998 | Carson et al. | 514/44 |

FOREIGN PATENT DOCUMENTS

| | | |
|---|---|---|
| EP | 092 574 B1 | 11/1983 |
| EP | 0468520 A3 | 1/1992 |
| EP | 0302758 B1 | 3/1994 |
| WO | WO 91/12811 | 9/1991 |
| WO | WO 92/03456 | 3/1992 |
| WO | WO 92/18522 | 10/1992 |
| WO | WO 92/21353 | 12/1992 |
| WO | WO 94/19945 | 9/1994 |
| WO | WO 95/05853 | 3/1995 |
| WO | WO 95/26204 | 10/1995 |
| WO | WO 96/02555 | 2/1996 |
| WO | WO 96/35782 | 11/1996 |
| WO | WO 97/12633 | 4/1997 |
| WO | WO 97/28259 | 8/1997 |
| WO | WO98/01538 | 1/1998 |
| WO | WO 98/14210 | 4/1998 |
| WO | WO 98/16247 A1 | 4/1998 |
| WO | WO 98/18810 | 5/1998 |
| WO | WO 98/32462 A1 | 7/1998 |
| WO | WO 98/37919 | 9/1998 |
| WO | WO 98/40100 | 9/1998 |
| WO | WO 98/52581 | 11/1998 |

OTHER PUBLICATIONS

Yamamoto et al, J. Immunol. 148: 4072 (1992).

Hamblin, T.J., "Ex vivo Activation and Retransfusion of White Blood Cells", *Therapeutic Cytaphersis,* 1990, pp. 249–266, No. 57.

Hartmann, G. et al., "CpG DNA: A potent signal for growth, activation, and maturation of human dendritic cells", *Proc. Natl. Acad. Sci. USA,* Aug. 1999, pp. 9305–9310, vol. 96.

Kataoka, T. et al., "Antitumor Activity of Synthetic Oligonucleotides with Sequences from cDNA Encoding Proteins of *Mycobacterium bovis* BCG", *Jpn. J. Cancer Res.,* Mar. 1992, pp. 244–247, vol. 83.

Wooldridge, J.E. et al., "Immunostimulatory Oligonucleotides Containing cpG Motifs Enhance the Efficacy of Monoclonal Antibody Therapy of Lymphoma", *Blood,* Apr. 15, 1997, pp. 2994–2998, vol. 89, No. 8.

Adya N et al., Expansion of CREB's DNA recognition specificity by Tax results from interaction with Ala–Ala–Arg at positions 282–284 near the conserved DNA–binding domain of CREB. *Proc Natl Acad Sci USA* 91(12):5642–6, Jun. 7, 1994.

Angier, N., Microbe DNA Seen as Alien By Immune System, *New York Times,* Apr. 11, 1995.

Azad RF et al., Antiviral Activity of a Phosphorothioate Oligonucleotide Complementary to RNA of the Human Cytomegalovirus Major Immediate–Early Region. *Antimicrobial Agents and Chemotherapy,* 37:1945–1954, Sep., 1993.

Azuma, Biochemical and Immunological Studies on Cellular Components of Tubercle Bacilli, *Kekkaku,* vol. 69, 9:45–55, 1992.

Ballas ZK et al., Induction of NK activity in murine and human cells by CpG motifs in oligodeoxynucleotides and bacterial DNA. *J Immunol* 157(5):1840–5, 1996.

Bayever, E., Systemic Administration of a Phosphorothioate Oligonucleotide with a Sequence Complementary to p53 for Acute Myelogenous leukemia and Myelodysplastic Syndrome: Initial Results of a Phase I Trial, *Antisense Res. & Dev.* (1993), 3:383–390.

Bennett RM et al., DNA binding to human leukocytes. Evidence for a receptor–mediated association, internalization, and degradation of DNA. *J Clin Invest* 76(6):2182–90, 1985.

(List continued on next page.)

*Primary Examiner*—James Martinell
(74) *Attorney, Agent, or Firm*—Wolf, Greenfield & Sacks, P.C.

(57) ABSTRACT

The present invention relates generally to methods and products for activating dendritic cells. In particular, the invention relates to oligonucleotides which have a specific sequence including at least one unmethylated CpG dinucleotide which are useful for activating dendritic cells. The methods are useful for in vitro, ex-vivo, and in vivo methods such as cancer immunotherapeutics, treatment of infectious disease and treatment of allergic disease.

21 Claims, 13 Drawing Sheets

OTHER PUBLICATIONS

Blaxter et al., Genes expressed in Brugia malayi infective third stage larvae. *Molecular and Biochemical Parasitology*, 77:77–93.

Boggs RT et al., Characterization and modulation of immune stimulation by modified oligonucleotides. *Antisense Nucleic Acid Drug Dev* 7(5):461–71, Oct. 1997.

Branda RF et al., Amplification of antibody production by phosphorothioate oligodeoxynucleotides. *J. Lab Clin Med* 128(3):329–38, Sep 1996.

Branda et al., Immune Stimulation by an Antisense Oligomer Complementary to the rev gene of HIV–1. *Biochemical Pharmacology*, vol. 45, 10:2037–2043, 1993.

Briskin M et al., Lipopolysaccharide–unresponsive mutant pre–B–cell lines blocked in NF–kappa B activation. *Mol Cell Biol* 10(1):422–5, Jan. 1990.

Chace, J. et al., Regulation of Differentiation in CD5+ and Conventional B Cells, *Clinical Immunology and Immunopathology*, (1993), 68:3:327–332.

Chang YN et al., The palindromic series I repeats in the simian cytomegalovirus major immediate–early promoter behave as both strong basal enhancers and cyclic AMP response elements. *J Virol* 64(1):264–77, Jan. 1990.

Chu RS et al., CpG oligodeoxynucleotides act as adjuvants that switch on T helper 1 (Th1) immunity. *J. Exp Med* 186(10):1623–31, Nov. 17, 1997.

Cowdery JS et al., Bacterial DNA induces NK cells to produce IFN–gamma in vivo and increases the toxicity of lipopolysaccharides. *J Immunol* 156(12):4570–5, Jun. 15, 1996.

Crosby et al., The Early Responses Gene FGFI–C Encodes a Zinc Finger Transcriptional Activator and is a Member of the GCGGGGGCG (GSG) Element–Binding Protein Family. *Mol. Cell. Biol.*, 2:3835–3841, 1991.

Crystal, Transfer of Genes to Humans: Early Lessons and Obstacles to Success. *Science*, vol. 270, pp. 404–410, 1995.

Englisch et al., Chemically Modified Oligonucleotides as Probes and Inhibitors, *Angew. Chem. Int. Ed. Engl.*, 30:613–629, 1991.

Erb KJ et al., Infection of mice with Mycobacterium bovis–Bacillus Calmette–Guerin (BCG) suppresses allergen–induced airway eosinophilia. *J Exp Med* 187(4):561–9, Feb. 16, 1998.

Etlinger, Carrier sequence selection—one key to successful vaccine, *Immunology Today*, vol. 13, 2:52–55, 1992.

Fox RI, Mechanism of action of hydroxychloroquine as an antirheumatic drug. *Chemical Abstracts*, 120:15, Abstract No. 182630 (Apr. 29, 1994).

Gura, T., Antisense Has Growing Pains. *Science* (1995), 270:575–576.

Hadden J et al., Immunostimulants. *TIPS*, (1993), 141:169–174.

Hadden J et al., Immunopharmacology, *JAMA*, (1992) 268:20:2964–2969.

Halpern MD et al., Bacterial DNA induces murine interferon–gamma production by stimulation of interleukin–12 and tumor necrosis factor–alpha. *Cell Immunol* 167(1):72–8, 1996.

Hatzfeld J., Release of Early Human Hematopoietic Progenitors from Quiescence by Antisense Transforming Growth Factor β1 or Rb Oligonucleotides, *J. Exp. Med.*, (1991) 174:925–929.

Highfield PE, Sepsis: the More, the Murkier. *Biotechnology*, 12:828, Aug. 12, 1994.

Hoeffler JP et al., Identification of multiple nuclear factors that interact with cyclic adenosine 3',5'–monophosphate response element–binding protein and activating transcription factor–2 by protein–protein interactions. *Mol Endocrinol* 5(2):256–66, Feb. 1991.

Iguchi–Ariga SM and Shaffner W, CpG methylation of the cAMP–responsive enhancer–promoter sequence TGACGTCA abolishes specific factor binding as well as transcriptional activation. *Genes Dev* 3(5):612–9, May 1989.

Iverson, P., et al., "Pharmacokinetics of an Antisense Phosphorothioate Oligodeoxynucleotide against reve from Human Immunodeficiency Virus Type 1 in the Adult male Rate Following Single Injections and Continuous Infusion", *Antisense Research and Development*, (1994), 4:43–52.

Ishikawa R et al., IFN induction and associated changes in splenic leukocyte distribution. *J Immunol* 150(9):3713–27, May 1, 1993.

Jakway JP et al., Growth regulation of the B lymphoma cell line WEHI–231 by anti–immunoglobulin, lipopolysaccharide, and other bacterial products. *J Immunol* 137(7):2225–31, Oct. 1, 1986.

Jaroszewski JW and Cohen JS, Cellular uptake of antisense oligonucleotides. *Adv Drug Delivery Rev* 6(3):235–50, 1991.

Kimura Y et al., Binding of Oligoguanylate to Scavenger Receptors Is Required for Oligonucleotides to Augment NK Cell Activity and Induce IFN, *J. Biochem.*, vol. 116, 6:991–994, 1994.

Kline JN et al., Immune redirection by CpG oligonucleotides. Conversion of a Th2 response to a Th1 response in a murine model of asthma. *J Invest Med* 45(3):282A, 1997.

Kline JN et al., CpG oligonucleotides can reverse as well as prevent Th2–mediated inflammation in a murine model of asthma. *J Invest Med* 45(7):298A, 1997.

Klinman DM et al., CpG motifs present in bacteria DNA rapidly induce lymphocytes to secrete interleukin 6, interleukin 12, and interferon gamma. *Proc Natl Acad Sci USA* 93(7):2879–83, 1996.

Krieg AM, An innate immune defense mechanism based on the recognition of CpG motifs in microbial DNA. *J Lab Clin Med*, 128(2):128–33, 1996.

Krieg AM et al., Uptake of oligodeoxyribonucleotides by lymphoid cells is heterogeneous and inducible. *Antisense Res Dev* 1(2):161–71, Summer 1991.

Krieg AM et al., Oligodeoxynucleotide modifications determine the magnitude of B cell stimulation by CpG motifs. *Antisense Nucleic Acid Drug Dev* 6(2):133–9, Summer 1996.

Krieg AM et al., "Modification of antisense phosphodiester oligodeoxynucleotides by a 5' cholesteryl moiety increases cellular association and improves efficacy", *Proc. Natl. Acad. Sci.*, (1993), 90:1048–1052.

Krieg AM et al., "CpG DNA: A Pathogenic Factor in Systemic Lupus Erythematosus?", *Journal of Clinical Immunology*, (1995) 15:6:284–292.

Krieg AM et al, Phosphorothioate Oligodeoxynucleotides; Antisense of Anti–Protein?, *Antisense Research and Development*, (1995), 5:241.

Krieg AM et al., "Leukocyte Stimulation by Oligodeoxynucleotides", *Applied Antisense Oligonucleotide Technology*, (1998), 431–448.

Krieg AM et al., CpG motifs in bacterial DNA trigger direct B–cell activation. *Nature* 374:546–9, 1995.

Krieg AM et al, "The role of CpG dinuleotides in DNA vaccines", Trends in Microbiology, vol. 6, pp. 23–37, Jan. 1998.

Krieg AM el al, A Role for Endogenous Retroviral Sequences in the Regulation of Lymphocyte Activation, the Journal of Immunology, vol. 143, 2448–2451.

Kuramoto et al., Oligonucleotide Sequences Required for Natural Killer Cell Activation, *Jpn. J. Cancer Res.,* 83:1128–1131, Nov. 1992.

Leonard et al., Conformation of Guanine 8–Oxoadenine Base Pairs in the Crystal Structure of d(CGCGAATT(08A)GCG). *Biochemistry,* 31(36):8415–8420, 1992.

Macfarlane DE and Manzel L, Antagonism of immunostimulatory CpG–oligodeoxynucleotides by quinacrine, chloroquine, and structurally related compounds. *J Immunol* 160(3):1122–31, Feb. 1, 1998.

Mastrangelo et al. *Seminars in Oncology.* vol. 23, 1:4–21, 1996.

Matson S and Krieg AM, Nonspecific suppression of [3H] thymidine incorporation by "control" oligonucleotides. *Antisense Res Dev* 2(4):325–30, Winter 1992.

McIntryre KW et al., A sense phosphorothioate oligonucleotide directed to the initiation codon of transcription factor NF–kappa B p65 causes sequence–specific immune stimulation. *Antisense Res Dev* 3(4):309–22, Winter 1993.

Messina et al., The Influence of DNA Structure on the in vitro Stimulation of Murine Lymphocytes by Natural and Synthetic Polynucleotide Antigens. *Cellular Immunology,* 147:148–157, 1993.

Messina et al., Stimulation of in vitro Murine Lymphocyte Proliferation by Bacterial DNA. *J. Immunol.,* vol. 147, 6:1759–1764, Sep. 15, 1991.

Mojcik, C., et al., "Administration of a Phosphorothioate Oligonucleotide Antisense Murine Endogenous Retroviral MDF env Causes Immune Effect in vivo in a Sequence–Specific Manner", *Clinical Immunology and Immunopathology,* (1993), 67:2:130–136.

Mottram et al., A novel CDC2–related protein kinase from leishmania mexicana LmmCRK1 is post–translationally regulated during the life cycle. *J. Biol. Chem.* 268:28, 21044–21052 (Oct. 1993).

New England BIOLABS 1988–1989 Catalog, item #1230.

Nyce JW and Metzger WJ, DNA antisense therapy for asthma in an animal model. *Nature* 385:721–725, Feb. 20, 1997.

Pisetsky, D., "Stimulation of in vitro proliferation of murine lymphocytes by synthetic oligodeoxynucleotides", *Molecular Biology Repairs,* (1993) 18:217–221.

Pisetsky et al., Stimulation of Murine Lymphocyte Proliferation by a Phosphorothioate Oligonucleotide with Antisense Activity for Herpes Simplex Virus. *Life Science,* vol. 54, pp. 101–107 (1994).

Pisetsky, The Immunological Properties of DNA, *The Journal of Immunology,* pp. 421–423 (1996).

Pisetsky, Immunological Consequences of Nucleic Acid Therapy, *Antisense Research and Development,* 5:219–225 (1995).

Raz E et al., Preferential induction of a Th1 immune response and inhibition of specific IgE antibody formation by plasmid DNA immunization. *Proc Natl Acad Sci USA* 93(10):5141–5, May 14, 1996.

Roman M et al., Immunostimulatory DNA Sequences function as T helper–1–promoting adjuvants. *Nat Med* 3(8):849–54, Aug. 1997.

Sato et al., Immunostimulatory DNA Sequences Necessary for Effective Intradermal Gene Immunization, *Science* vol. 273, pp. 352–354, 1996.

Schnell et al., Identification and characterization of a *Saccharomyces cerevisiae* gene (PAR1) conferring resistance to iron chelators. *Eur. J. Biochem.,* 200:487–493.

Schwartz DA et al., CpG motifs in bacterial DNA cause inflammation in the lower respiratory tract. *J Clin Invest* 100(1):68–73, Jul. 1, 1997.

Shirakawa T et al., The inverse association between tuberculin responses and atopic disorder. *Science* 275(5296):77–9, Jan. 3, 1997.

Sparwasser T et al., Macrophages sense pathogens via DNA motifs: induction of tumor necrosis factor–alpha–mediated shock. *Eur J Immunol* 27(7):1671–9, Jul. 1997.

Stein CA et al., Oligonucleotides as inhibitors of gene expression: a review. *Cancer Research,* 48:2659–2668, 1988.

Stull et al., Antigene, Ribozyme, and Aptamer Nucleic Acid Drugs: Progress and Prospects, *Pharmaceutical Res.,* vol. 12, 4:465–483, 1995.

Subramanian et al., Theoretical Considerations on the "Spine of Hydration" in the Minor Groove of d(CGCGAATTCGCG) d(GCGCTTAAGCGC): Monte Carlo Computer Simulation. *Proc. Nat'l. Acad. Sci. USA,* 85:1836–1840, 1988.

Tanaka T et al., An antisense Oligonucleotide complementary to a sequence in IG2b increases G2b germline transcripts stimulates B cell DNA synthesis and inhibits immunoglobulin secretion. *J. Exp. Med.,* 175:597–607, 1992.

Tokunaga T et al., Synthetic Oligonucleotides with Particular Base Sequences form the cDNA Encoding Proteins of *Myobacterium bovis* BCG Induce Interferons and Activate Natural Killer Cells, *Microbiol. Immunol.,* vol. 36, 1:55–66, 1992.

Tokunaga et al., A Synthetic Single–Stranded DNA, Ply (dG, dC), Induces Interferon $\alpha/\beta$ and $-\gamma$, Augments Natural Killer Activity and Suppresses Tumor Growth. *Jpn. J. Cancer Res.,* 79:682–686, Jun. 1988.

Uhlmann et al., Antisense Oligonucleotides: A New Therapeutic Principle. *Chemical Reviews,* 90:543–584, 1990.

Wagner RW, Gene inhibition using antisense oligodeoxynucleotides. *Nature,* 372:L333–335, 1994.

Wallace et al., Oligonucleotide probes for the screening of recombinant DNA libraries. *Methods in Enzymology,* 152:432–442 (1987).

Weiss R., Upping the Antisense Ante: Scientists bet on profits from reverse genetics. *Science,* 139:108–109, 1991.

Whalen R, DNA Vaccines for Emerging Infection Diseases: What If?, *Emerging Infectious Disease,* vol. 2, 3:168–175, 1996.

Wu GY et al., Receptor–mediated gene delivery and expression in vivo. *J. Biol. Chem.,* 263:14621–14624, 1988.

Wu–Pong S., Oligonucleotides: Opportunities for Drug Therapy and Research. *Pharmaceutical Technology,* 18:102–114, 1994.

Yamamoto S et al., DNA from bacteria, but not from vertebrates, induces interferons, activates natural killer cells and inhibits tumor growth. *Microbiol Immunol* 36(9):983–97, 1992.

Yamamoto S et al., In vitro augmentation of natural killer cell activity and production of interferon–alpha/beta and—gamma with deoxyribonucleic acid fraction from *Mycobacterium bovis* BCG. *Jpn J Cancer Res* 79:866–73, Jul. 1988.

Yamamoto S., Mode of Action of Oligonucleotide Fraction Extracted from Mycobacterium bovis BCG, *Kekkaku,* vol. 69, 9:29–32, 1994.

Yamamoto S et al., Unique Palindromic Sequences in Synthetic Oligonucleotides are Required to Induce INF and Augment INF–Mediated Natural Killer Activity. *J. Immunol.,* vol. 148, 12:4072–4076, Jun. 15, 1992.

Yamamoto T et al., Ability of Oligonucleotides with Certain Palindromes to Induce Interferon Production and Augment Natural Killer Cell Activity is Associated with Their Base Length. *Antisense Res. and Devel.,* 4:119–123, 1994.

Yamamoto et al., Lipofection of Synthetic Oligodeoxyribonucleotide Having a Palindromic Sequence AACGTT to Murine Splenocytes Enhances Interferon Production and Natural Killer Activity. *Microbiol. Immunol,* vol. 38, 10:831–836, 1994.

Yamamoto T et al., Synthetic Oligonucleotides with Certain Palindromes Stimulate Interferon Production of Human Peripheral Blood Lymphocytes in vitro. *Jpn. J. Cancer Res.,* 85:775–779, 1994.

Yi, Ae–Kyung et al., IFN–γ Promotes IL–6 and IgM Secretion in Response to CpG Motifs in Bacterial DNA and Oligonucleotides, *The Journal of Immunology,* pp. 558–564 (1996).

Yi, Ae–Kyung et al., Rapid Immune Activation by CpG Motifs in Bacterial DNA, *The Journal of Immunology,* pp. 5394–5402 (1996).

Zhao Q et al., Stage–specific oligonucleotide uptake in murine bone marrow B–cell precursors. *Blood* 84(11):3660–6, Dec. 1, 1994.

Zhao Q et al., Comparison of cellular binding and uptake of antisense phosphodiester, phosphorothioate, and mixed phosphorothioate and methylphosphonate oligonucleotides. *Antisense Res Dev* 3(1):53–66, Spring 1993.

Aggarwal SK et al., Cell–surface–associated nucleic acid in tumorigenic cells made visible with platinum–pyrimidine complexes by electron microscopy. *Proc Natl Acad Sci USA* 72(3):928–32, 1975.

Bennett SR et al., Help for cytoxic–T–cell responses is mediated by CD40 signalling. *Nature* 393(6684):478–80, Jun. 4, 1998.

Constant P et al., Stimulation of human gamma delta T cells by nonpeptidic mycobacterial ligans. *Science* 264:267–70, 1994.

DeMatos P et al., Pulsing of dendritic cells with cell lysates from either B16 melanoma or MCA–106 fibrosarcoma yields equally effective vaccines against B16 tumors in mice. *J. Surg Oncol* 68(2):79–91, Jun. 1998.

Doe, B., et al., Induction of cytotoxic T lymphocytes by intramuscular immunization with plasmid DNA is facilitated by bone marrow–derived cells, Proc Natl, Acad, Sci, 93:8578–8583, (1996).

Engleman EG, Dendritic cells: potential role in cancer therapy. *Cytotechnology* 25(1–3):1–8, 1997.

Ewel CH et al., Polyinosinic–polycytidylic acid complexed with poly–L–lysine and carboxymethylcellulose in combination with interleukin 2 in patients with cancer: clinical and immunological effects. *Cancer Res* 52(11):3005–10, 1992.

Feldbush, T., et al. , "Lymphokine–Like Activity of 8–<ercaptoguanosine: Induction of T and B Cell Differentiation", The American Association of Immunologists, 134:5:3204–3211, (1985).

Fields RC et al., Murine dendritic cells pulsed with whole tumor lysates mediate potent antitumor immune responses in vitro and in vivo. *Proc Natl Acad Sci USA* 95(16):9482–7, Aug. 4, 1998.

Garrigan K et al., Functional Comparison of Spleen Dendritic Cells and Dendritic Cells Cultured In Vitro From Bone Marrow Precursors, *Blood* 88(9):3508–3512, Nov. 1, 1996.

Gilboa E et al., Immunotherapy of cancer with dendritic–cell–based vaccines. *Cancer Immunol Immunother* 46:82–87, 1998.

Gluckman JC et al., In vitro generation of human dendritic cells and cell therapy. *Cytokines Cell Mol Ther* 3(3):187–96, Sep. 1997.

Goodman MG, Mechanism of synergy between T cell signals and C8–substituted guanine nucleosides in humoral immunity: B lymphotrophic cytokines induce responsiveness to 8–mercaptoguanosine. *J Immunol* 136(9):3335–40, 1986.

Guery JC and Adorini L, Dendritic cells are the most efficient in presenting endogenous naturally processed self–epitopes to class II–restricted T cells. *J Immunol* 154(2):536–44, Jan. 15, 1995.

Gura, T., Antisense Has Growing Pains. *Science* (1995), 270:575–576.

Hamblin, T., et al., "Ex vivo activation and retransfusion of white blood cells", *Therapeutic Cytapheresis,* 249–266, (1990).

Hsu FJ et al., Vaccination of patients with B–cell lymphoma using autologous antigen–pulsed dendritic cells. *Nat Med* 2(1):52–8, Jan. 1996.

Jakob T et al., Activation of cutaneous dendritic cells by CpG–containing oligodeoxynucleotides: a role for dendritc cells in the augmentation of Th1 responses by immunostimulatory DNA. *J Immunol* 161(6):3042–9, Sep. 15, 1998.

Koo GC et al., Activation of murine natural killer cells and macrophages by 8–bromoguanosine. *J Immunol* 140(9):3249–52, 1988.

Krown SE, Interferons and interferon inducers in cancer treatment. *Semin Oncol* 13(2):207–17, 1986.

Lanzavecchia A., License to kill. *Nature* 393(6684):413–4, Jun. 4, 1998.

Lerner RA et al., Membrane–associated DNA in the cytoplasm of diploid human lymphocytes. *Proc Natl Acad Sci USA* 68(6):1212–6, 1971.

Ludewig B et al., Dendritic Cells Efficiently Induce Protective Antiviral Immunity. *Journal of Virology,* 72(5):3812–3818, May 1998.

Nair SK et al., Regression of tumors in mice vaccinated with professional antigen–presenting cells pulsed with tumor extracts. *Int J Cancer* 70(6):706–15, Mar. 17, 1997.

Nestle FO et al., Vaccination of melanoma patients with peptide– or tumor lysate–pulsed dendritic cells. *Nat Med* 4(3):328–32, Mar. 1998.

O'Doherty U et al., Dendritic cells freshly isolated from human blood express CD4 and mature into typical immunostimulatory dendritic cells after culture in monocyte–conditioned medium. *J Exp Med* 178(3):1067–76, Sep. 1, 1993.

Okada H et al., Bone marrow–derived dendritic cells pulsed with a tumor–specific peptide elicit effective anti–tumor immunity against intracranial neoplasms. *Int J Cancer* 78(2):196–201, Oct. 5, 1998.

Ridge JP et al., A conditioned dendritic cell can be a temporal bridge between a CD4+ T–helper and a T–killer cell. *Nature* 393(6684):474–8, Jun. 4, 1998.

Robinson PR et al., Development Aspects of Dendritic Cells In Vitro and In Vivo. *Leukemia and Lymphoma,* 29:477–490, Jul. 1997.

Romani et al., Generation of mature dendritic cells from human blood. An improved method with special regard to clinical applicability. *J Immunol Methods* 196(2):137–51, Sep. 27, 1996.

Rosenberg SA et al., Immunologic and therapeutic evaluation of a synthetic peptide vaccine for the treatment of patients with metastatic melanoma. *Nat Med* 4(3):321–7, Mar. 1998.

Schoenberger SP et al., T–cell help for cytotoxic T lymphocytes is mediated by CD40–CD40L interactions. *Nature* 393(6684):480–3, Jun. 4, 1998.

Sparwasser T et al., Bacterial DNA and immunostimulatory CpG oligonucleotides trigger maturation and activation of murine dendritic cells. *Eur. J Immunol* 28(6):2045–54, Jun. 1998.

Steinman RM, Dendritic cells and immune–based therapies. *Exp Hematol* 24(8):859–62, Jul. 1996.

Talmadge JE et al., Immunomodulatory effects in mice of polyinosinic–polycytidylic acid complexed with poly–L–lysine and carboxymethylcellulose. *Cancer Res* 45(3):1058–65, 1985.

Tjoa BA et al., Evaluation of phase I/II clinical trials in prostate cancer with dendritic cells and PSMA peptides. *Prostate* 36(1):39–44, Jun. 15, 1998.

Tsubata T et al., B–cell apoptosis induced by antigen receptor crosslinking is blocked by a T–cell signal through CD40. *Nature* 364(6438):645–8, Aug. 12, 1993.

Uhlmann et al., Antisense Oligonucleotides: A New Therapeutic Principle. *Chemical Reviews,* 90:543–584, 1990.

van Schooten WCA et al., Biological properties of dendritic cells: implications to their use in the treatment of cancer. *Mol Medicine Today,* 254–260, Jun. 1997.

Wiltrout RH et al., Immunomodulation of natural killer cells by polyribonucleotides. *J Biol Response Mod* 4(5):512–7, 1985.

Yang S et al., Immunotherapeutic potential of tumor antigen–pulsed and unpulsed dendritic cells generated from murine bone marrow. *Cell Immunol* 179(1):84–95, Jul. 10, 1997.

Thompson, R., et al., "Lymphokine–Activated Killer (LAK) Cells", *J. of Immunology,* 145:10:3524–3531, (1990).

Grouard, G., et al., The Enigmatic Plasmacytoid T Cells Develp into Dendritic Cell siwht Interleukin (IL)–3 and CD 40–Ligand, *J Exp. Med.,* 185:6:1101–1111, (1997).

GMCSF + CpG

CpG

GMCSF

GMCSF + non-CpG

+CpG

-CpG

+CpG

+CpG

IMMUNOSTIMULATORY NUCLEIC ACID MOLECULES FOR ACTIVATING DENDRITIC CELLS

RELATED APPLICATIONS

This application is a continuation-in-part of U.S. Ser. No. 08/960,774, filed Oct. 30, 1997 now U.S. Pat. No. 6,239,116, which is a continuation-in-part of U.S. Ser. No. 08/738,652, filed Oct. 30, 1996 and now U.S. Pat. No. 6,207,646, and which application is a continuation-in-part of U.S. Ser. No. 08/386,063, filed Feb. 7, 1995 and now U.S. Pat. No. 6,194,388, and which application is a continuation-in-part of U.S. Ser. No. 08/276,358, filed Jul. 15, 1994 and which is abandoned.

FIELD OF THE INVENTION

The present invention relates generally to methods and products for activating dendritic cells. In particular, the invention relates to oligonucleotides which have a specific sequence including at least one unmethylated CpG dinucleotide which are useful for activating dendritic cells.

BACKGROUND OF THE INVENTION

In the 1970s, several investigators reported the binding of high molecular weight DNA to cell membranes (Lerner, R. A., et al., 1971, *Proc. Natl. Acad. Sci. USA*, 68:1212; Aggarwal, S. K., et al., 1975, *Proc. Natl. Acad. Sci. USA*, 72:928). In 1985, Bennett et al. presented the first evidence that DNA binding to lymphocytes is similar to a ligand receptor interaction; binding is saturable, competitive, and leads to DNA endocytosis and degradation into oligonucleotides (Bennett, R. M., et al., *J. Clin. Invest.*, 76:2182). Like DNA, oligodeoxyribonucleotides (ODNs) are able to enter cells in a saturable, sequence independent, and temperature and energy dependent fashion (reviewed in Jaroszewski, J. W., et al. and J. S. Cohen, 1991, *Advanced Drug Delivery Reviews*, 6:235; Akhtar, et al., 1992, in: "Gene Regulation: Biology of Antisense RNA and DNA," R. P. Erickson, Eds, Raven Press, Ltd., New York, p. 133; and Zhao, et al., 1994, *Blood*, 84:3660). No receptor for DNA or ODN uptake has yet been cloned, and it is not yet clear whether ODN binding and cell uptake occurs through the same or a different mechanism from that of high molecular weight DNA.

Lymphocyte ODN uptake has been shown to be regulated by cell activation. Spleen cells stimulated with the B cell mitogen LPS had dramatically enhanced ODN uptake in the B cell population, while spleen cells treated with the T cell mitogen ConA showed enhanced ODN uptake by T but not B cells (Krieg, A. M., et al., 1991, *Antisense Research and Development*, 1:161).

Several polynucleotides have been extensively evaluated as biological response modifiers. Perhaps the best example is poly(IC) which is a potent inducer of interferon (IFN) production as well as a macrophage activator and inducer of NK activity (Talmadge, J. E., et al., 1985, *Cancer Res.*, 45:1058; Wiltrout, et al., 1985, *J. Biol. Resp. Mod.*, 4:512; Krown, S. E., 1986, *Sem. Oncol.*, 13:207; and Ewel, C. H., et al., 1992, *Canc. Res.*, 52:3005). It appears that this murine NK activation may be due solely to induction of IFN-β secretion (Ishikawa, R., and C. A. Biron, 1993, *J. Immunol.*, 150:3713). This activation was specific for the ribose sugar since deoxyribose was ineffective. Its potent in vitro antitumor activity led to several clinical trials using poly(IC) complexed with poly-L-lysine and carboxymethylcellulose (to reduce degradation by RNAse) (Talmadge, et al., cited supra; Wiltrout, et al., cited supra; Krown, et al., cited supra, and Ewel, et al., cited supra). Unfortunately, toxic side effects has thus far prevented poly(IC) from becoming a useful therapeutic agent.

Guanine ribonucleotides substituted at the C8 position with either a bromine or a thiol group are B cell mitogens and may replace "B cell differentiation factors" (Feldbush, T. L., and Z. K. Ballas, 1985, *J. Immunol.*, 134:3204; and Goodman, M. J., 1986, *J. Immunol.*, 136:3335). 8-mercaptoguanosine and 8-bromoguanosine also can substitute for the cytokine requirement for the generation of MHC restricted CTL (Feldbush, T. L., cited supra), augment murine NK activity (Koo, G.C., et al., 1988, *J. Immunol.*, 140:3249) and synergize with IL-2 in inducing murine LAK generation (Thompson, R. A., and Z. K. Ballas, 1990, *J. Immunol.*, 145:3524). The NK and LAK augmenting activities of these C8-substituted guanosines appear to be due to their induction of IFN (Thompson, cited supra). Recently a 5' triphosphorylated thymidine produced by a mycobacterium was found to be mitogenic for a subset of human γδ T cells (Constant, P., et al., 1994, *Science*, 264:267). This report indicated the possibility that the immune system may have evolved ways to preferentially respond to microbial nucleic acids.

Several observations suggest that certain DNA structures may also have the potential to activate lymphocytes. For example, Bell, et al. reported that nucleosomal protein-DNA complexes (but not naked DNA) in spleen cell supernatants caused B cell proliferation and immunoglobulin secretion (Bell, D. A., et al., 1990, *J. Clin. Invest.*, 85:1487). In other cases, naked DNA has been reported to have immune effects. For example, Messina, et al. have recently reported that 260–800 bp fragments of poly(bG).(dC) and poly(dG, dC) were mitogenic for B cells (Messina, J. P., et al., 1993, *Cell. Immunol.*, 147:148). Tokunaga, et al. have reported that poly(dg, dc) induces the γ-IFN and NK activity (Tokunaga, et al., 1988, *Jpn. J Cancer Res.*, 79:682). Aside from such artificial homopolymer sequences, Pisetsky, et al. reported that pure mammalian DNA has no detectable immune effects, but that DNA from certain bacteria induces B cell activation and immunoglobulin secretion (Messina, et al., 1991, *J. Immunol.*, 147:1759). Assuming that these data did not result from some unusual contaminant, these studies suggested that a particular structure or other characteristic of bacterial DNA renders it capable of triggering B cell activation. Investigations of microbacterial DNA sequences have demonstrated that ODN, which contains certain palindrome sequences can activate NK cells (Yamamoto, et al., 1992, *J. Immunol.*, 148:4072; and Kuramoto, et al., 1992, *Jpn. J. Cancer Res.*, 83:1128).

Several phosphorothioate modified ODN have been reported to induce in vitro or in vivo B cell stimulation (Tanaka, et al., 1992, *J. Exp. Med.*, 175:597; Branda, R. S., et al., 1993, *Biochem. Pharmacol.*, 45:2037; McIntyre, K., et al., 1993, *Antisense Res. Develop.*, 3:309; and Pisetesky, et al., 1994, *Life Sciences*, 54:101). These reports do not suggest a common structure motif or sequence element in these ODN that might explain their effects.

Dendritic cells are considered to be the most potent professional antigen-presenting cells (APC) (Guery, J. C., et al., 1995, *J. Immunol.*, 154:536). Dendritic cells capture antigen and present them as peptide fragments to T cells, stimulating T cell dependent immunity. These powerful APCs have been found in skin, blood, dense tissue, and mucosa, and spleen. Several studies have demonstrated that after human dendritic cells which are isolated from peripheral blood are presented peptide antigen they can be used to stimulate and expand antigen specific CD4+ and CD8+ T cells, in vitro and ex vivo (Engleman, E. G., 1997, *Cytotechnology*, 25:1). Several clinical trials are currently underway, based on these findings, using ex vivo manipulation of dendritic cells to generate specific anti-tumor dendritic cells for reimplantation. There has been a growing interest in using dendritic cells ex vivo as tumor or infectious disease vaccine adjuvants (Nestle OF, et al., "Vaccination of melanoma patients with peptide- or tumor lysate-pulsed dendritic cells", *Nat Med*, 1998; 4: 328–332; Rosenberg S A, et al., "Immunologic and therapeutic evaluation of a synthetic peptide vaccine for the treatment of patients with metastatic melanoma", *Nat Med*, 1998; 4:321–327; Hsu F J, et al., "Vaccination of patients with B-cell lymphoma using autologous antigen-pulsed dendritic cells", *Nat Med*, 1996; 2: 52–58; Tjoa BA, et al., "Evaluation of phase I/II clinical trials in prostate cancer with dendritic cells and PSMA peptides", *Prostate*, 1998; 36: 39–44. Numerous animal models demonstrate conclusively that ex vivo generated DC pulsed with protein antigen can be successfully applied for the immunotherapy of cancer and infectious diseases. (Fields R C, et al., "Murine dendritic cells pulsed with whole tumor lysates mediate potent antitumor immune responses in vitro and in vivo", *Proc Natl Acad Sci, USA*, 1998; 95: 9482–9487; Okada H, et al., "Bone marrow-derived dendritic cells pulsed with a tumor-specific peptide elicit effective anti-tumor immunity against intracranial neoplasms", *Int J Cancer*, 1998; 78: 196–201; Su H, et al., "Vaccination against chlamydial genital tract infection after immunization with dendritic cells pulsed ex vivo with nonviable Chlamydiae", *J Exp Med*, 1998; 188: 809–818; DeMatos P., et al., "Pulsing of dendritic cells with cell lysates from either B16 melanoma or MCA-106 fibrosarcoma yields equally effective vaccines against B 16 tumors in mice", *J Surg Oncol*, 1998; 68: 79–91; Yang S, et al., "Immunotherapeutic potential of tumor antigen-pulsed and unpulsed dendritic cells generated from murine bone marrow", *Cell Immunol*, 1997; 179: 84–95; Nair S K, et al., "Regression of tumors in mice vaccinated with professional antigen- presenting cells pulsed with tumor extracts", *Int J Cancer*, 1997; 70: 706–715.

SUMMARY OF THE INVENTION

As described in co-pending parent patent application U.S. Ser. No. 08/960,774 the vertebrate immune system has the ability to recognize the presence of bacterial DNA based on the recognition of so-called CpG-motifs, unmethylated cytidine-guanosine dinucleotides within specific patterns of flanking bases. According to these disclosures CpG functions as an adjuvant and is as potent at inducing B-cell and T-cell responses as the complete Freund's adjuvant, but is preferable since CpG induces a higher Th1 response and is less toxic. Alum, the adjuvant which is used routinely in human vaccination, induces the less favorable Th2 response. Compared to alum, CpG is a more effective adjuvant. The combination of CpG and alum was found to produce a synergistic adjuvant effect.

CpG oligonucleotides also show adjuvant effects towards various immune cells. For instance, CpG enhances the efficacy of monoclonal antibody therapy, thus functioning as an effective immune adjuvant for antigen immunization in a B cell lymphoma model. Cytotoxic T cell responses to protein antigen also are induced by CpG. Furthermore, the presence of immunostimulatory DNA sequences in plasmids was found to be necessary for effective intradermal gene immunization.

It was discovered according to an aspect of the invention that the adjuvant activity of CpG is based on the direct activation of dendritic cells by CpG. Potent immunostimulatory CpG oligonucleotides and control oligonucleotides were found to cause dramatic changes in dendritic cells isolated from peripheral blood by immunomagnetic cell sorting. CpG oligonucleotides provided excellent Dendritic cell survival, differentiation, activation and maturation, and were superior to the combination of GM-CSF and LPS. In fact, the combination of CpG and GM-CSF produced unexpected synergistic effects on the activation of dendritic cells. The invention thus encompasses both CpG oligonucleotides and the combination of CpG oligonucleotides and cytokines such as GM-CSF as well as in vitro, ex vivo, and in vivo methods of activating dendritic cells for various assays and immunotherapeutic strategies.

In one aspect the invention is a method for activating a dendritic cell. The method includes the steps of contacting a dendritic cell with an isolated nucleic acid containing at least one unmethylated CpG dinucleotide wherein the nucleic acid is from about 8–80 bases in length in an amount effective to activate a dendritic cell. In one embodiment the dendritic cell is an isolated dendritic cell.

The isolated nucleic acid is one which contains at least one unmethylated CpG dinucleotide and which is from about 8–80 bases in length. In one embodiment the unmethylated CpG dinucleotide has a formula:

$$5'N_1X_1CGX_2N_2 3'$$

wherein at least one nucleotide separates consecutive CpGs; $X_1$ is adenine, guanine, or thymine; $X_2$ is cytosine, adenine, or thymine; N is any nucleotide and $N_1+N_2$ is from about 0–25 nucleotides. In another embodiment the unmethylated CpG dinucleotide has a formula:

$$5'N_1X_1X_2CGX_3X_4N3'$$

wherein at least one nucleotide separates consecutive CpGs; $X_1X_2$ is selected from the group consisting of TpT, CpT, TpC, and ApT; $X_3X_4$ is selected from the group consisting of GpT,GpA, ApA and ApT; N is any nucleotide and $N_1+N_2$ is from about 0–25 nucleotides. In a preferred embodiment $N_1$ and $N_2$ of the nucleic acid do not contain a CCGG quadmer or more than one CCG or CGG trimer. In an illustrative embodiment the isolated nucleic acid is selected from the group consisting of SEQ ID NOS. 20, 24, and 38–46. In another embodiment the isolated nucleic acid is SEQ ID NO.: 84 or 85.

In yet another embodiment the nucleotide of the isolated nucleic acid has a phosphate backbone modification, such as, for example, a phosphorothioate or phosphorodithioate modification. In one embodiment the phosphate backbone modification occurs at the 5' end of the nucleic acid. Preferably the phosphate backbone modification occurs at the first two internucleotide linkages of the 5' end of the nucleic acid. According to another embodiment the phosphate backbone modification occurs at the 3' end of the nucleic acid. Preferably, the phosphate backbone modification occurs at the last five internucleotide linkages of the 3' end of the nucleic acid.

The method for activating the dendritic cell may be performed in vitro, ex vivo, or in vivo. The method in some aspects is a method for cancer immunotherapy, treating an infectious disease, or treating an allergy. When these methods are performed ex vivo they are performed by administering an activated dendritic cell that expresses a specific cancer antigen, microbial antigen or allergen to a subject in need thereof, wherein the activated dendritic cell is prepared by the methods described above. In a preferred embodiment the isolated nucleic acid is administered to a human subject.

In other embodiments the method includes the step of contacting the dendritic cell with a cytokine selected from the group consisting of GM-CSF, IL-4, TNFα, INF-γ, IL-6, Flt3 ligand, and IL-3. In yet other embodiments the method includes the step of contacting the dendritic cell with an antigen prior to the isolated nucleic acid.

The invention in another aspect is an isolated antigen-expressing dendritic cell population produced by the process of: exposing an isolated dendritic cell to an antigen; contacting the isolated dendritic cell with an isolated nucleic acid containing at least one unmethylated CpG dinucleotide wherein the isolated nucleic acid is from about 8–80 bases in length; and allowing the isolated dendritic cell to process and express the antigen.

The isolated nucleic acid is one which contains at least one unmethylated CpG dinucleotide and which is from about 8–80 bases in length. In one embodiment the unmethylated CpG dinucleotide has a formula:

$$5'N_1X_1CGX_2N_23'$$

wherein at least one nucleotide separates consecutive CpGs; $X_1$ is adenine, guanine, or thymine; $X_2$ is cytosine, adenine, or thymine; N is any nucleotide and $N_1+N_2$ is from about 0–25 nucleotides. In another embodiment the unmethylated CpG dinucleotide has a formula:

$$5'NX_1X_2CGX_3X_4N3'$$

wherein at least one nucleotide separates consecutive CpGs; $X_1X_2$ is selected from the group consisting of TpT, CpT, TpC, and ApT; $X_3X_4$ is selected from the group consisting of GpT, GpA, ApA and ApT; N is any nucleotide and $N_1+N_2$ is from about 0–25 nucleotides. In a preferred embodiment $N_1$ and $N_2$ of the nucleic acid do not contain a CCGG quadmer or more than one CCG or CGG trimer. In an illustrative embodiment the isolated nucleic acid is selected from the group consisting of SEQ ID Nos. 20, 24 and 38–46. In another embodiment the isolated nucleic acid is SEQ ID NO.: 84 or 85.

In yet another embodiment the nucleotide of the isolated nucleic acid has a phosphate backbone modification, such as, for example, a phosphorothioate or phosphorodithioate modification. In one embodiment the phosphate backbone modification occurs at the 5' end of the nucleic acid. Preferably the phosphate backbone modification occurs at the first two internucleotide linkages of the 5' end of the nucleic acid. According to another embodiment the phosphate backbone modification occurs at the 3' end of the nucleic acid. Preferably, the phosphate backbone modification occurs at the last five internucleotide linkages of the 3' end of the nucleic acid.

According to another embodiment the isolated antigen-expressing dendritic cell is prepared by contacting the isolated dendritic cell with a cytokine selected from the group consisting of GM-CSF, IL-4, TNFα, INF-γ, IL-6, Flt3 ligand, and IL-3.

In yet another embodiment the isolated antigen-expressing dendritic cell is prepared by contacting the isolated dendritic cell with the antigen prior to the isolated nucleic acid.

The invention in another aspect is a composition, including an effective amount for synergistically activating a dendritic cell of an isolated nucleic acid containing at least one unmethylated CpG dinucleotide wherein the nucleic acid is from about 8–80 bases in length; and an effective amount for synergistically activating a dendritic cell of a cytokine selected from the group consisting of GM-CSF, IL-4, TNFα, Flt3 ligand, and IL-3. In an illustrative embodiment the cytokine is GM-CSF. In another embodiment the composition also includes an antigen, such as, for example a cancer antigen, a microbial antigen, or an allergen.

In another aspect the invention is a screening assay for identifying compounds that are effective for preventing dendritic cell maturation. The assay includes the following steps: contacting an immature dendritic cell with an isolated nucleic acid containing at least one unmethylated CpG dinucleotide wherein the nucleic acid is from about 8–80 bases in length; exposing the dendritic cell to a putative drug; and detecting the presence or absence of a maturation marker on the dendritic cell, wherein the absence of the maturation marker indicates that the putative drug is an effective compound for preventing dendritic cell maturation. In one illustrative embodiment the maturation marker is CD83.

The invention in another aspect is a method for generating a high yield of dendritic cells. The method includes the following steps administering an isolated nucleic acid containing at least one unmethylated CpG dinucleotide wherein the nucleic acid is from about 8–80 bases in length in an amount effective for activating dendritic cells to a subject; allowing the isolated nucleic acid to activate dendritic cells of the subject; and isolating dendritic cells from the subject.

In another aspect the invention is a method for producing a CD40 expressing dendritic cell. The method includes the following steps: contacting a dendritic cell with an isolated nucleic acid containing at least one unmethylated CpG dinucleotide wherein the nucleic acid is from about 8–80 bases in length in an amount effective to produce a CD40 expressing dendritic cell.

A method for causing maturation of a dendritic cell is provided according to another aspect of the invention. The method includes the step of contacting a dendritic cell with an isolated nucleic acid containing at least one unmethylated CpG dinucleotide wherein the nucleic acid is from about 8–80 bases in length in an amount effective to cause maturation of the dendritic cell.

Each of the limitations of the invention can encompass various embodiments of the invention. It is, therefore, anticipated that each of the limitations of the invention involving any one element or combinations of elements can be included in each aspect of the invention.

DETAILED DESCRIPTION OF THE INVENTION

Figure 1:
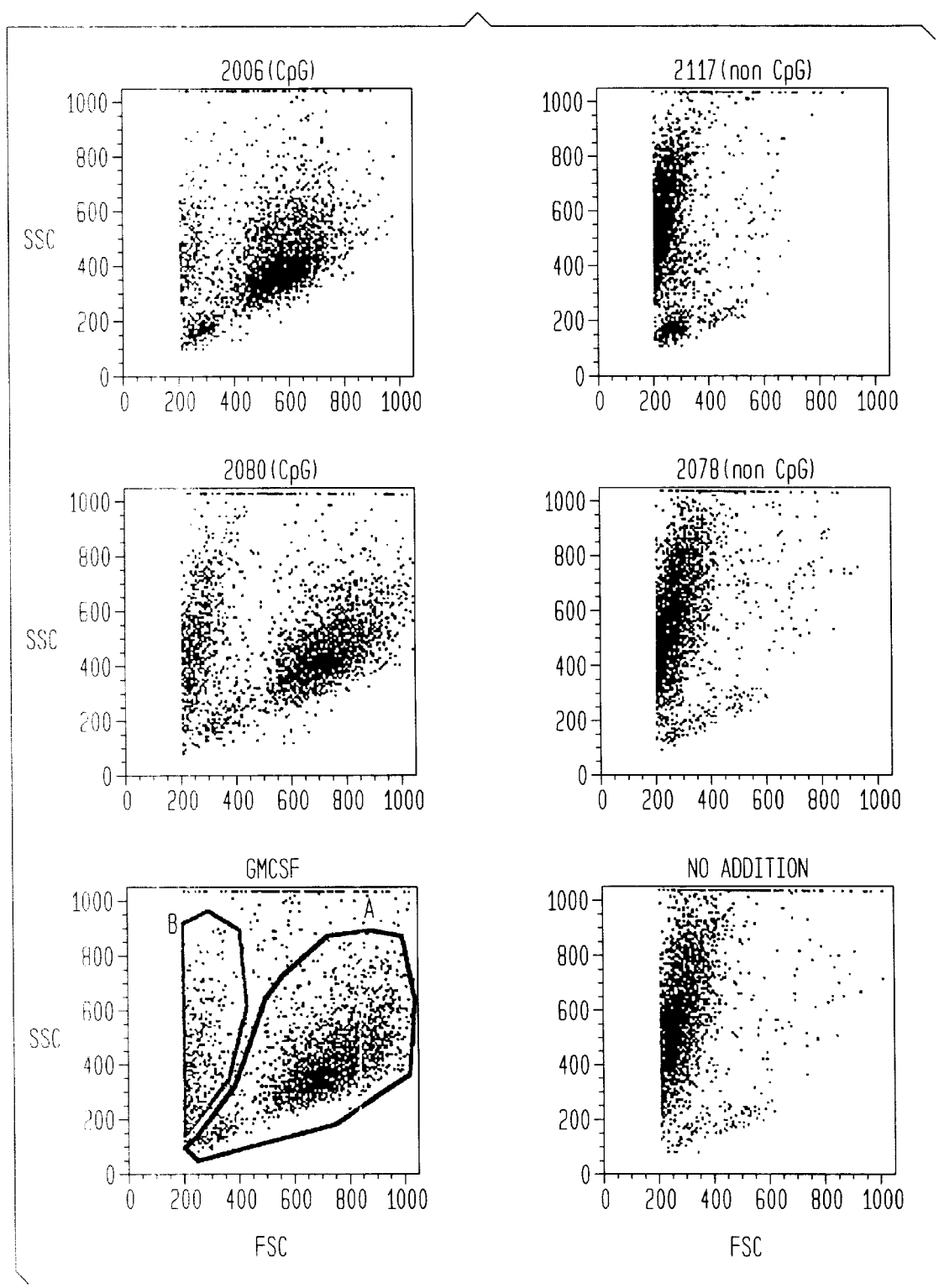
FIG. 1 shows FACS chart depicting CpG oligonucleotide promoted survival of dendritic precursor cells. Freshly isolated dendritic precursor cells were incubated for 2 days in the presence of either oligonucleotides or GMCSF (800 U/ml). Flow cytometric analysis of morphology (forward scatter, FSC; sideward scatter, SSC) showed that CpG oligonucleotides (2006: CpG phosphorothioate oligonucleotide, 1×2 μg/ml, 2080 CpG phosphodiester oligonucleotide, 3×30 μg/ml) promote survival of dendritic precursor cells, while the non CpG controls (2117: 2006 with methylated CpG; 2078: identical to 2080 but GpCs instead of CpGs) showed no positive effect on cell survival compared to the sample without oligonucleotides and GMCSF (no addition). Morphologically (FSC and SSC), viable cells were found in region A, now viable cells in region B (regions drawn in lower left dot plot).

Dendritic cells form the link between the innate and the acquired immune system by presenting antigens as well as through their expression of pattern recognition receptors which detect microbial molecules like LPS in their local environment. It has been discovered according to the invention that CpG has the unique capability to promote cell survival, differentiation, activation and maturation of dendritic cells. In fact dendritic precursor cells isolated from human blood by immunomagnetic cell sorting develop morphologic and functional characteristics of dendritic cells during a two day incubation with GM-CSF. Without GM-CSF these cells undergo apoptosis. It was discovered according to the invention that CpG was superior to GM-CSF in promoting survival and differentiation of dendritic cells (MHC II expression, cell size, granularity). As shown in the Examples below, the CpG phosphorothioate oligonucleotide 2006 (2 μg/ml) induced the expression of ICAM-1 (CD54) by 3.6-fold (p=0.02; n=5), the co-stimulatory molecule B7-2 (CD86) by 2.4-fold (p=0.03; n=5) and CD40 by 4.1-fold (p=0.04; n=4). The combination of GM-CSF and 2006 showed a synergistic induction of CD86 and CD40, and an additive effect for CD54. Induction of CD54, CD86 and CD40 by 2006 alone was higher compared to either GM-CSF alone or GM-CSF combined with LPS. Electron microscopy revealed major ultrastructural changes of dendritic cells in response to CpG, indicating that these cells were differentiated. Additionally CpG was found to induce maturation of dendritic cells. CpG oligonucleotide 2006 was superior to GM-CSF and LPS at inducing maturation marker CD83. A synergistic maturation effect was observed when CpG oligonucleotide 2006 and GM-CSF were used together.

All effects of CpG on dendritic cells were CpG-specific as shown by control oligonucleotides with methylated CpG motifs and oligonucleotides containing GpC instead of CpG. Thus, the addition of a CpG oligonucleotide is sufficient for improving survival, differentiation, activation and maturation of human dendritic cells. Since dendritic cells form the link between the innate and the acquired immune system the ability to activate dendritic cells with CpG supports the use of CpG-based strategies for immunotherapy against disorders such as cancer and allergic or infectious diseases.

Adjuvants are nonspecific stimulators of the immune response. They are considered to be nonspecific because they only produce an immune response in the presence of an antigen. Adjuvants allow much smaller doses of antigen to be used and are essential to inducing a strong antibody response to soluble antigens (Harlow and Lane, *Antibodies: A Laboratory Manual*, Cold Spring Harbor, N.Y., current edition). It is shown according to the invention that CpG functions as an adjuvant by activating dendritic cells. CpG is a particularly useful adjuvant in humans because of its low toxicity. Many potent adjuvants in mice or other animals, like the Freunds complete adjuvant, cannot be used in humans due to toxicity. Additionally, as demonstrated in the examples below, CpG activates and matures human primary blood dendritic cells where other known adjuvants such as LPS fail to do so. Furthermore, CpG is known to induce a Th1 immune response which is believed to be superior to the immune response induced by alum, the adjuvant currently used in humans.

Thus the use of CpG allows the generation of mature dendritic cells from peripheral blood within two days in a well defined system. The application of CpG for this purpose is superior to GM-CSF, which is currently used for this purpose. CpG oligonucleotides have a longer half life, are less expensive, and show a greater magnitude of immune effects. The combination of CpG and GM-CSF shows synergistic activity for the induction of co-stimulatory molecules (CD86, CD40).

The invention relates in one aspect to methods and products for activating dendritic cells for in vitro, ex vivo and in vivo purposes. It was demonstrated according to the invention that CpG oligodeoxyribonucleotides are potent activators of dendritic cells. Dendritic cells are believed to be essential for the initiation of primary immune responses in immune cells in vivo. It was discovered, according to the invention, that CpG oligodeoxyribonucleotide was capable of activating dendritic cells to initiate primary immune responses in T cells, similar to an adjuvant. It was also discovered the CpG ODN induces the production of large amounts of IL-12 in dendritic cells, indicating its propensity to augment the development of Th1 immune responses in vivo. The findings that CpG oligonucleotides were sufficient for survival, differentiation, activation, and maturation of human dendritic cells demonstrate the potent adjuvant activity of CpG and provide the basis for the use of CpG oligodeoxyribonucleotides as immunotherapeutics in the treatment of disorders such as cancer, infectious diseases, and allergy. In one aspect, the invention is a method for activating a dendritic cell by contacting the dendritic cell with an isolated nucleic acid containing at least one unmethylated CpG dinucleotide, wherein the nucleic acid is from about 8–80 bases in length.

The methods and products of the invention are useful for a variety of purposes. For instance, the invention is particularly useful as an adjuvant for stimulating specific B and T cell responses to immunization. This is accomplished by contacting immature dendritic cells with an isolated nucleic acid containing at least one unmethylated CpG dinucleotide to cause the dendritic cell to become activated and to mature. The activated dendritic cell is then incubated with resting T cells to cause activation of the T cells in order to initiate a primary immune response. In some cases the dendritic cell is also contacted with an antigen. Dendritic cells efficiently internalize process and present the soluble tumor-specific antigen to which it is exposed. The process of internalizing and presenting antigen causes rapid upregulation of the expression of major histocompatibility complex (MHC) and costimulatory molecules, the production of cytokines, and migration toward lymphatic organs where they are believed to be involved in the activation of T cells.

One specific use for the CpG nucleic acids of the invention is to activate dendritic cells for the purpose of enhancing a specific immune response against cancer antigens. The immune response may be enhanced using ex vivo or in vivo techniques. An "ex vivo" method as used herein is a method which involves isolation of an immature dendritic cell from a subject, manipulation of the cell outside of the body, and reimplantation of the manipulated cell into a subject. The ex vivo procedure may be used on autologous or heterologous cells, but is preferably used on autologous cells. In preferred embodiments, the immature dendritic cells are isolated from peripheral blood or bone marrow, but may be isolated from any source of dendritic cells. When the ex vivo procedure is performed to specifically produce dendritic cells active against a specific cancer antigen, the dendritic cells may be exposed to the cancer antigen in addition to the CpG. In other cases the dendritic cell may have already been exposed to antigen but may not be expressing the antigen on the surface efficiently. Activation will dramatically increase antigen processing. The activated dendritic cell then presents the cancer antigen on its surface. When returned to the subject, the activated dendritic cell expressing the cancer antigen activates T cells in vivo which are specific for the cancer antigen. Ex vivo manipulation of dendritic cells for the purposes of cancer immunotherapy have been described in several references in the art, including Engleman, E. G., 1997, *Cytotechnology*, 25:1; Van Schooten, W., et al., 1997, *Molecular Medicine Today*, June, 255; Steinman, R. M., 1996, *Experimental Hematology*, 24, 849; and Gluckman, J. C., 1997, *Cytokines, Cellular and Molecular Therapy*, 3:187. The ex vivo activation of dendritic cells of the invention may be performed by routine ex vivo manipulation steps known in the art, but with the use of CpG as the activator.

The dendritic cells may also be contacted with CpG using in vivo methods. In order to accomplish this, CpG is administered directly to a subject in need of immunotherapy. The CpG may be administered in combination with an antigen or may be administered alone. In some embodiments, it is preferred that the CpG be administered in the local region of the tumor.

An "antigen" as used herein is a molecule capable of provoking an immune response. Antigens include but are not limited to cells, cell extracts, polysaccharides, polysaccharide conjugates, lipids, glycolipids, carbohydrate, viruses, and viral extracts. A "cancer antigen" as used herein is a peptide associated with a tumor or cancer cell surface and which is capable of provoking an immune response when expressed on the surface of an antigen presenting cell in the context of an MHC molecule. Cancer antigens can be prepared from cancer cells either by preparing crude extracts of cancer cells, for example, as described in Cohen, et al., 1994, *Cancer Research*, 54:1055, by partially purifying the antigens, by recombinant technology, or by de novo synthesis of known antigens. Cancer antigens are isolated from a tumor or cancer (e.g. tumors of the brain, lung (e.g. small cell and non-small cell), ovary, breast, prostate, colon, as well as other carcinomas and sarcomas).

The isolated dendritic cell is contacted with CpG and exposed to an antigen. Although either step may be performed first or the steps may be performed simultaneously, in one preferred embodiment the antigen is exposed to the immature dendritic cell before the cell is contacted with the CpG. It is believed that the antigen is taken up by the dendritic cell and then when the dendritic cell is contacted with the CpG, that the dendritic cell is activated to process and present the antigen. Preferably, the antigen is exposed to the cell within 48 hours of adding CpG. In a more preferred embodiment, the dendritic cell is exposed to the antigen within 24 hours of the CpG.

The antigen is exposed to the dendritic cell. As used herein, the term "exposed to" refers to either the active step of contacting the dendritic cell with an antigen in culture under conditions which promote the uptake and processing of the antigen, the passive exposure of antigen to the dendritic cell in vivo prior to isolation of the dendritic cell, or the transfection of the dendritic cell with a gene encoding the antigen, to cause processing and presentation of the antigen through the cytosolic/class I pathway. Methods for the active exposure of dendritic cells to antigen are well-known in the art. In general, purified dendritic cells are pulsed with antigen under culture conditions which promote the uptake and processing of the antigen such that the antigen will be expressed on the cell surface in association with either class I or class II MHC. Methods for transfecting dendritic cells with DNA encoding an antigen are also well-known to those of ordinary skill in the art and require only routine experimentation.

The compositions and methods of the invention are also useful for treating infectious diseases. An infectious disease, as used herein, is a disease arising from the presence of a foreign microorganism in the body. CpG is used to stimulate an antigen specific dendritic cell which can activate a T cell response against an antigen of the microorganism. The methods are accomplished in the same way as described above for the tumor except that the antigen is specific for a microorganism using a microbial antigen. A "microbial antigen" as used herein is an antigen from a microorganism and includes but is not limited to infectious virus, infectious bacteria, and infectious fungi.

Examples of infectious virus include: *Retroviridae* (e.g. human immunodeficiency viruses, such as HIV-1 (also referred to as HTLV-III, LAV or HTLV-III/LAV, or HIV-III; and other isolates, such as HIV-LP; Picornaviridae (e.g. polio viruses, hepatitis A virus; enteroviruses, human coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronaviridae (e.g. coronaviruses); Rhabdoviridae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviruses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus); Poxviridae (variola viruses, vaccinia viruses, pox viruses); and Iridoviridae (e.g. African swine fever virus); and unclassified viruses (e.g. the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

Examples of infectious bacteria include: *Helicobacter pyloris, Borelia burgdorferi, Legionella pneumophilia,* Mycobacteria sps (e.g. *M. tuberculosis, M. avium, M. intracellulare, M. kansasii, M. gordonae), Staphylococcus aureus, Neisseria gonorrhoeae, Neisseria meningitidis, Listeria monocytogenes, Streptococcus pyogenes* (Group A Streptococcus), *Streptococcus agalactiae* (Group B Streptococcus), Streptococcus (viridans group), *Streptococcus faecalis, Streptococcus bovis*, Streptococcus (anaerobic sps.), *Streptococcus pneumoniae*, pathogenic Campylobacter sp., Enterococcus sp., *Haemophilus influenzae, Bacillus anthracis, corynebacterium diphtheriae, corynebacterium* sp., *Erysipelothrix rhusiopathiae, Clostridium perfringens, Clostridium tetani, Enterobacter aerogenes, Klebsiella pneumoniae, Pasturella multocida*, Bacteroides sp., *Fusobacterium nucleatum, Streptobacillus moniliformis, Treponema Treponema pertenue*, Leptospira, and *Actinomyces israelli.*

Examples of infectious fungi include: *Cryptococcus neoformans, Histoplasma capsulatum, Coccidioides immitis, Blastomyces dermatitidis, Chlamydia trachomatis, Candida albicans.* Other infectious organisms (i.e., protists) include: *Plasmodium falciparum* and *Toxoplasma gondii.*

The methods of the invention are also useful for treating allergic diseases. The methods are accomplished in the same way as described above for the tumor immunotherapy and treatment of infectious diseases except that the antigen is specific for an allergen. Currently, allergic diseases are generally treated by the injection of small doses of antigen followed by subsequent increasing dosage of antigen. It is believed that this procedure produces a memory immune response to prevent further allergic reactions. These methods, however, are associated with the risk of side effects such as an allergic response. The methods of the invention avoid these problems.

An "allergen" refers to a substance (antigen) that can induce an allergic or asthmatic response in a susceptible subject. The list of allergens is enormous and can include pollens, insect venoms, animal dander, dust, fungal spores and drugs (e.g. penicillin). Examples of natural, animal and plant allergens include proteins specific to the following genuses: Canine (*Canis familiaris*); Dermatophagoides (e.g. *Dermatophagoides farinae*); Felis (*Felis domesticus*); Ambrosia (*Ambrosia artemiisfolia*; Lolium (e.g. *Lolium perenne* or *Lolium multiflorum*); Cryptomeria (*Cryptomeria*

*japonica*); Alternaria (*Alternaria alternata*); Alder; Alnus (*Alnus gultinoasa*); Betula (*Betula verrucosa*); Quercus (Quercus alba); Olea (*Olea europa*); Artemisia (*Artemisia vulgaris*); Plantago (e.g. Plantago lanceolata); Parietaria (e.g. Parietaria officinalis or *Parietaria judaica*); Blattella (e.g. *Blattella germanica*); Apis (e.g. *Apis multiflorum*); Cupressus (e.g. Cupressus sempervirens, *Cupressus arizonica* and *Cupressus macrocarpa*); Juniperus (e.g. *Juniperus sabinoides, Juniperus virginiana, Juniperus communis* and *Juniperus ashei*); Thuya (e.g. Thuya orientalis); Chamaecyparis (e.g. *Chamaecyparis obtusa*); Periplaneta (e.g. *Periplaneta americana*); Agropyron (e.g. *Agropyron repens*); Secale (e.g. *Secale cereale*); Triticum (e.g. *Triticum aestivum*); Dactylis (e.g. *Dactylis glomerata*); Festuca (e.g. *Festuca elatior*); Poa (e.g. *Poa pratensis* or *Poa compressa*); Avena (e.g. *Avena sativa*); Holcus (e.g. *Holcus lanatus*); Anthoxanthum (e.g. *Anthoxanthum odoratum*); Arrhenatherum (e.g. *Arrhenatherum elatius*); Agrostis (e.g. *Agrostis alba*); Phleum (e.g. *Phleum pratense*); Phalaris (e.g. *Phalaris arundinacea*); Paspalum (e.g. *Paspalum notatum*); Sorghum (e.g. *Sorghum halepensis*); and Bromus (e.g. *Bromus inermis*).

An "allergy" refers to acquired hypersensitivity to a substance (allergen). Allergic conditions include but are not limited to eczema, allergic rhinitis or coryza, hay fever, bronchial asthma, urticaria (hives) and food allergies, and other atopic conditions. A subject having an allergic reaction is a subject that has or is at risk of developing an allergy.

"Asthma" refers to a disorder of the respiratory system characterized by inflammation, narrowing of the airways and increased reactivity of the airways to inhaled agents. Asthma is frequently, although not exclusively associated with atopic or allergic symptoms.

In addition to the treatment of active disorders, the methods and products of the invention can be used as a prophylactic vaccine. In this case, the CpG nucleic acid sequence is administered in vivo, preferably in the presence of an antigen or dendritic cells are prepared ex vivo and administered.

The CpG oligonucleotides of the invention are immunostimulatory molecules. An "immunostimulatory nucleic acid molecule" refers to a nucleic acid molecule, which contains an unmethylated cytosine, guanine dinucleotide sequence (i.e. "CpG DNA" or DNA containing a cytosine followed by guanosine and linked by a phosphate bond) and stimulates (e.g. has a mitogenic effect on, or induces or increases cytokine expression by) a dendritic cell. An immunostimulatory nucleic acid molecule can be double-stranded or single-stranded. Generally, double-stranded molecules are more stable in vivo, while single-stranded molecules have increased immune activity.

A "nucleic acid" or "DNA" means multiple nucleotides (i.e. molecules comprising a sugar (e.g. ribose or deoxyribose) linked to a phosphate group and to an exchangeable organic base, which is either a substituted pyrimidine (e.g. cytosine (C), thymine (T) or uracil (U)) or a substituted purine (e.g. adenine (A) or guanine (G)). As used herein, the term refers to ribonucleotides as well as oligodeoxyribonucleotides. The term shall also include polynucleosides (i.e. a polynucleotide minus the phosphate) and any other organic base containing polymer. Nucleic acid molecules can be obtained from existing nucleic acid sources (e.g. genomic or cDNA), but are preferably synthetic (e.g. produced by oligonucleotide synthesis).

In one preferred embodiment the invention provides an isolated immunostimulatory nucleic acid sequence containing a CpG motif represented by the formula:

$$5'N_1X_1CGX_2N_23'$$

wherein at least one nucleotide separates consecutive CpGs; $X_1$ is adenine, guanine, or thymine; $X_2$ is cytosine, adenine, or thymine; N is any nucleotide and $N_1+N_2$ is from about 0–25 nucleotides.

In another embodiment the invention provides an isolated immunostimulatory nucleic acid sequence containing a CpG motif represented by the formula:

$$5'NX_1X_2CGX_3X_4N3'$$

wherein at least one nucleotide separates consecutive CpGs; $X_1X_2$ is selected from the group consisting of TpT, CpT, TpC, and ApT; $X_3X_4$ is selected from the group consisting of GpT, GpA, ApA and ApT; N is any nucleotide and $N_1+N_2$ is from about 0–25 nucleotides. In a preferred embodiment $N_1$ and $N_2$ of the nucleic acid do not contain a CCGG quadmer or more than one CCG or CGG trimer.

Preferably the immunostimulatory nucleic acid sequences of the invention include $X_1X_2$ selected from the group consisting of GpT, GpG, GpA and ApA and $X_3X_4$ is selected from the group consisting of TpT, CpT and GpT. For facilitating uptake into cells, CpG containing immunostimulatory nucleic acid molecules are preferably in the range of 8 to 30 bases in length. However, nucleic acids of any size (even many kb long) are immunostimulatory if sufficient immunostimulatory motifs are present, since larger nucleic acids are degraded into oligonucleotides inside of cells. Preferred synthetic oligonucleotides do not include a CCGG quadmer or more than one CCG or CGG trimer at or near the 5' and/or 3' terminals and/or the consensus mitogenic CpG motif is not a palindrome. Prolonged immunostimulation can be obtained using stabilized oligonucleotides, where the oligonucleotide incorporates a phosphate backbone modification, as discussed in more detail below. For example, the modification is a phosphorothioate or phosphorodithioate modification. More particularly, the phosphate backbone modification occurs at the 5' end of the nucleic acid for example, at the first two nucleotides of the 5' end of the nucleic acid. Further, the phosphate backbone modification may occur at the 3' end of the nucleic acid for example, at the last five nucleotides of the 3' end of the nucleic acid.

Preferably the immunostimulatory CpG DNA is in the range of between 8 to 30 bases in size when it is an oligonucleotide. Alternatively, CpG dinucleotides can be produced on a large scale in plasmids, which after being administered to a subject are degraded into oligonucleotides. Preferred immunostimulatory nucleic acid molecules (e.g. for use in increasing the effectiveness of a vaccine or to treat an immune system deficiency by stimulating an antibody (i.e. humoral response in a subject) have a relatively high stimulation index with regard to B cell, dendritic cell and/or natural killer cell responses (e.g. cytokine, proliferative, lytic or other responses).

A "nucleic acid delivery complex" shall mean a nucleic acid molecule associated with (e.g. ionically or covalently bound to; or encapsulated within) a targeting means (e.g. a molecule that results in higher affinity binding to target cell (e.g. dendritic cell surfaces and/or increased cellular uptake by target cells). Examples of nucleic acid delivery complexes include nucleic acids associated with: a sterol (e.g. cholesterol), a lipid (e.g. a cationic lipid, virosome or liposome), or a target cell specific binding agent (e.g. a ligand recognized by target cell specific receptor). Preferred complexes must be sufficiently stable in vivo to prevent significant uncoupling prior to internalization by the target cell. However, the complex should be cleavable under appropriate conditions within the cell so that the nucleic acid is released in a functional form.

"Palindromic sequence" shall mean an inverted repeat (i.e. a sequence such as ABCDEE'D'C'B'A' in which A and A' are bases capable of forming the usual Watson-Crick base pairs. In vivo, such sequences may form double-stranded structures.

A "stabilized nucleic acid molecule" shall mean a nucleic acid molecule that is relatively resistant to in vivo degradation (e.g. via an exo- or endo-nuclease). Stabilization can be a function of length or secondary structure. Unmethylated CpG containing nucleic acid molecules that are tens to hundreds of kbs long are relatively resistant to in vivo degradation. For shorter immunostimulatory nucleic acid molecules, secondary structure can stabilize and increase their effect. For example, if the 3' end of a nucleic acid molecule has self-complementarity to an upstream region, so that it can fold back and form a sort of stem loop structure, then the nucleic acid molecule becomes stabilized and therefore exhibits more activity.

Preferred stabilized nucleic acid molecules of the instant invention have a modified backbone. It was shown according to the invention that modification of the oligonucleotide backbone provided enhanced activity of the CpG molecules of the invention when administered in vivo. CpG constructs, including at least two phosphorothioate linkages at the 5' end of the oligodeoxyribonucleotide and multiple phosphorothioate linkages at the 3' end, preferably 5, provided maximal activity and protected the oligodeoxyribonucleotide from degradation by intracellular exo- and endo-nucleases. Other modified oligodeoxyribonucleotides include phosphodiester modified oligodeoxyribonucleotide, combinations of phosphodiester and phosphorothioate oligodeoxyribonucleotide, methylphosphonate, methylphosphorothioate, phosphorodithioate, and combinations thereof. Each of these combinations and their particular effects on immune cells is discussed in more detail in copending PCT patent ppplication U.S. Ser. No. 08/960,774, filed on Oct. 30, 1997, the entire contents of which is hereby incorporated by reference. It is believed that these modified oligodeoxyribonucleotides may show more stimulatory activity due to enhanced nuclease resistance, increased cellular uptake, increased protein binding, and/or altered intracellular localization.

Both phosphorothioate and phosphodiester oligonucleotides containing CpG motifs were active in dendritic cells. However, based on the concentration needed to induce CpG specific effects, the nuclease resistant phosphorothioate backbone CpG oligonucleotides were more potent (2 μg/ml for the phosphorothioate vs. a total of 90 μg/ml for phosphodiester). In the concentration used in this study, phosphorothioate oligonucleotides without CpG motifs showed no background stimulatory activity such as that described earlier for high phosphorothioate oligonucleotide concentrations.

Other stabilized nucleic acid molecules include: nonionic DNA analogs, such as alkyl- and aryl-phosphates (in which the charged phosphonate oxygen is replaced by an alkyl or aryl group), phosphodiester and alkylphosphotriesters, in which the charged oxygen moiety is alkylated. Nucleic acid molecules which contain diol, such as tetraethyleneglycol or hexaethyleneglycol, at either or both termini have also been shown to be substantially resistant to nuclease degradation.

As used herein, the term "vector" refers to a nucleic acid molecule capable of transporting another nucleic acid to which it has been linked. Preferred vectors are those capable of autonomous replication and expression of nucleic acids to which they are linked (e.g. an episome). Vectors capable of directing the expression of genes to which they are operatively linked are referred to herein as "expression vectors." In general, expression vectors of utility in recombinant DNA techniques are often in the form of "plasmids" which refer generally to circular double-stranded DNA loops which, in their vector form, are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

A "subject" shall mean a human or vertebrate animal including a dog, cat, horse, cow, pig, sheep, goat, chicken, monkey, rat, and mouse.

The nucleic acid sequences of the invention which are useful for stimulating dendritic cells are those broadly described above. Exemplary sequences include but are not limited to those sequences shown in Table 1–7 as well as TCCATGTCGCTCCTGATGCT (SEQ ID NO: 42), TCCATGTCGTTCCTGATGCT (SEQ ID NO: 43), TCGTCGTTGTCGTTGTCGTT (SEQ ID NO: 83); TCGTCGTTTTGTCGTTTTGTCGTT (SEQ ID NO: 84), TCGTCGTTGTCGTTTTGTCGTT (SEQ ID NO: 85), GCGTGCGTTGTCGTTGTCGTT (SEQ ID NO: 86), TGTCGTTTGTCGTTTGTCGTT (SEQ ID NO: 88), TGTCGTTGTCGTTGTCGTT (SEQ ID NO: 90) TCGTCGTCGTCGTT (SEQ ID NO: 91), TCCTGTCGT-TCCTTGTCGTT (SEQ ID NO: 73), TCCT-GTCGTTTTTGTCGTT (SEQ ID NO: 75), TCGTCGCT-GTCTGCCCTTCTT (SEQ ID NO: 76), TCGTCGCTGTTGTCGTTTCTT (SEQ ID NO: 77), TCGTCGTTTTGTCGTTTTGTCGTT (SEQ ID NO: 84), TCGTCGTTGTCGTTTTGTCGTT (SEQ ID NO: 85) TGTCGTTGTCGTTGTCGTT (SEQ ID NO: 90), TCCAT-GACGTTCCTGACGTT (SEQ ID NO: 97), GTCG(T/C)T and TGTCG(T/C)T.

The stimulation index of a particular immunostimulatory CpG DNA can be tested in various immune cell assays. Preferably, the stimulation index of the immunostimulatory CgG DNA with regard to B cell proliferation is at least about 5, preferably at least about 10, more preferably at least about 15 and most preferably at least about 20 as determined by incorporation of $^3$H uridine in a murine B cell culture, which has been contacted with 20 μM of ODN for 20 h at 37° C. and has been pulsed with 1 μCi of $^3$H uridine; and harvested and counted 4 h later as described in detail in copending PCT patent application U.S. Ser. No. 08/960,774. For use in vivo, for example to treat an immune system deficiency by stimulating a cell-mediated (local) immune response in a subject, it is important that the immunostimulatory CpG DNA be capable of effectively inducing cytokine secretion by dendritic cells.

Preferred immunostimulatory CpG nucleic acids should effect at least about 500 pg/ml of TNF-α, 15 pg/ml IFN-γ, 70 pg/ml of GM-CSF 275 pg/ml of IL-6, 200 pg/ml IL-12, depending on the therapeutic indication, as determined by the assays described in the Examples. Other preferred immunostimulatory CpG DNAs should effect at least about 10%, more preferably at least about 15% and most preferably at least about 20% YAC-1 cell specific lysis or at least about 30, more preferably at least about 35 and most preferably at least about 40% 2C11 cell specific lysis.

It was found that the motifs that stimulate murine cells best differ from those that are more effective with human cells. Certain CpG oligodeoxynucleotides are poor at activating human cells (oligodeoxyribonucleotide 1707, 1708, which contain the palindrome forming sequences GACGTC and CACGTG, respectively).

The CpG oligonucleotides are used to induce survival, activation, maturation, and differentiation of dendritic cells. A dendritic cell has its ordinary meaning in the art and includes immature dendritic cells, mature dendritic cells, antigen expressing dendritic cells, non antigen expressing cells, precursor and progenitor dendritic cells. Dendritic cells are known to express different panels of cell surface molecules at different stages of development as described in more detail below. An activated dendritic cell is a dendritic cell which capable of efficiently processing antigen. Activated dendritic cells may or may not have already taken up antigen. A mature dendritic cell as used herein is a dendritic cell which expresses CD83 on the surface.

Dendritic cells useful according to the invention may be isolated from any source as long as the cell is capable of being activated by CpG to produce an active antigen expressing dendritic cell. Several in vivo sources of immature dendritic cells may be used according to the methods of the invention. For instance bone marrow dendritic cells and peripheral blood dendritic cells are both excellent sources of immature dendritic cells that are activated by CpG. Other sources may easily be determined by those of skill in the art without requiring undue experimentation, by for instance, isolating a primary source of dendritic cells and testing activation by CpG in vitro (e.g., using assays described in the Examples section). The invention also encompasses the use of any immature dendritic cells maintained in culture as a cell line as long as the cell is capable of being activated by CpG. Such cell types may be routinely identified using standard assays known in the art.

It was discovered according to the invention, that not all sources of dendritic cells that are known to be activated by cytokines to produce antigen presenting dendritic cells are capable of being activated by CpG. For instance, monocyte-derived dendritic cells are not activated by CpG. Recently, the method of monocyte-derived dendritic cells has attracted major attention because the incubation of purified CD14-positive monocytes with GM-CSF and IL-4 and subsequent maturation with conditioned medium or TNF provides large numbers of dendritic cells within one week. Romani N, et al. *J Immunol Methods* 1996; 196: 137–151. Since these cells tend to de-differentiate into macrophages in the absence of IL-4 Hausser G, et al. *Immunobiology* 1997; 197: 534–542, these dendritic cells may not resemble the physiologic situation. Although these cells are highly responsive to LPS it was discovered that monocyte-derived Dendritic cells do not respond to CpG (see Examples). It was also demonstrated that human monocytes, while highly sensitive to LPS, show a minor and delayed response to CpG.

Peripheral blood dendritic cells isolated by immunomagnetic cell sorting, which are activated by CpG, represent a more physiologic cell population of dendritic cells than monocyte derived dendritic cells. Immature dendritic cells comprise approximately 1–3% of the cells in the bone marrow and approximately 10–100 fold less in the peripheral blood. Peripheral blood cells can be collected using devices well-known in the art, e.g., Haemonetics model v. 50 apheresis device (Haemonetics, Braintree, Mass.). Red blood cells and neutrophils are removed from the blood by centrifugation. The mononuclear cells located at the interface are isolated. Methods for isolating CD4+ dendritic cells from peripheral blood have been described O'Doherty U, et al. *J Exp Med* 1993; 178: 1067–1076 and are set forth in the Examples. In the presence of GM-CSF these cells differentiate to dendritic cells with characteristic cellular processes within two days. Differentiation is accompanied by an increase in cell size, granularity and MHC class II expression, which can be easily followed using flow cytometry. Freshly isolated dendritic cells cultured in the absence of GM-CSF rapidly undergo apoptosis. Strikingly, in the presence of CpG oligonucleotides without addition of GM-CSF, both cell survival and differentiation is markedly improved compared to GM-CSF. In the presence of CpG, dendritic cells form cell clusters which when examined by ultrastructural techniques such as electron microscopy revealed characteristic dense multilamellar intracytoplasmic bodies and multi-vesicular structures, which were not present in dendritic cells incubated with GM-CSF. Scanning electron microscopy showed long veil and sheet-like processes thought to be used for intercellular interactions, and an irregular cell shape. In contrast, cells incubated with GM-CSF were round-shaped and had only minor cellular processes. In addition to promoting survival and differentiation of dendritic cells, a single addition of CpG oligonucleotide led to activation as represented by upregulation of the co-stimulatory molecules ICAM-1 (CD54), B7-2 (CD86) and CD40. The combination of CpG oligonucleotide and GM-CSF enhanced the expression of CD86 and CD40 synergistically, proving that activation is not due to CpG-induced GM-CSF.

In addition to activating dendritic cells CpG was capable of causing maturation of the dendritic cells. Maturation is assessed by the appearance of CD83, a specific marker for mature human dendritic cells. The presence of CpG alone for two days was sufficient to cause maturation of a variable percentage of the cells and the combination of GM-CSF and CpG was found to act synergistically to cause maturation of an even greater number of cells.

Each of the effects observed by culturing cells in the presence of CpG, improved survival, differentiation, activation and maturation of dendritic cells, were CpG specific since control oligonucleotides with methylated CpGs and oligonucleotides with GpC instead of CpGs were inactive. Additionally, CpG was superior to LPS in inducing both activation and maturation.

CD40-mediated activation of dendritic cells plays a key role for the induction of cytotoxic T-cells from naive T-cells. The profound changes observed in CpG-stimulated dendritic cells are similar to those seen after activation by CD40 Lanzavecchia A. Licence to kill. *Nature* 1998; 393: 413–414. Recently the central role of CD40 ligation for "superactivation" of dendritic cells has been identified. Lanzavecchia A. Licence to kill. *Nature* 1998; 393: 413–414; Schoenberger S P, et al. *Nature* 1998; 393: 480–483; Ridge J P, Di Rosa F, Matzinger P. *Nature* 1998; 393: 474–478. Bennett S R, et al. *Nature* 1998; 393: 478–480. While TNF and LPS activate dendritic cells by upregulation of co-stimulatory molecules, CD40 ligation on dendritic cells is required for the dendritic cell-dependent induction of cytotoxic T-cells from naive T-cells. CD40 ligand present on the surface of activated T helper cells provides this signal under physiologic circumstances. In addition to the data presented herein the data presented in the parent application indicate that CpG may be substitutes for CD40 ligation on dendritic cells. CD40 and CpG perform a number of parallel actions. First, CpG and CD40 both activate c-Jun NH2-terminal kinase and p38, but do not activate the extracellular receptor kinase in B cells. Second, CD40 and CpG are each sufficient to induce proliferation of B-cells. Finally, both CD40 and CpG activate NK cells in an IL-12 dependent manner.

The ability of CpG to activate human dendritic cells differs from that of murine dendritic cells. It has also been discovered that CpG upregulates MHC class II and co-stimulatory molecules on murine Langerhans cells. In another study similar changes were described for murine bone marrow-derived Dendritic cells. Sparwasser T, et al. *Eur J Immunol* 1998; 28: 2045–2054. In both studies the efficacy of CpG to induce co-stimulatory molecules does not exceed the effects seen for LPS, to which monocytic cells are highly sensitive. Murine monocytes/macrophages are known to secrete high amounts of inflammatory cytokines in response to CpG. Since the murine cell preparation may include other myelomonocytic cells in the analysis as well a secondary indirect effect of CpG on Dendritic cells in these cell preparations may have contributed to the described activation of Dendritic cells.

It has been shown according to the invention that purified human blood dendritic cells are highly sensitive to CpG, while their response to LPS is barely detectable. The LPS concentration used in this study (10 ng/ml) is 10-fold higher than the concentration found to induce maximal cytokine secretion in human monocytes (1 ng/ml). It is important to note that murine macrophages are approximately 1000-fold less sensitive to LPS than human macrophages. In contrast to human macrophages, the low sensitivity of human blood dendritic cells to LPS and the high sensitivity to CpG is striking.

Certain Unmethylated CpG Containing Nucleic Acids Were Initially Demonstrated to Have B Cell Stimulatory Activity as Shown In Vitro and In Vivo In the course of investigating the lymphocyte stimulatory effects of two antisense oligonucleotides specific for endogenous retroviral sequences, using protocols described in the attached Examples 1 and 2 of Co-pending parent patent application U.S. Ser. No. 08/960,774, it was surprisingly found that two out of twenty-four "controls" (including various scrambled, sense, and mismatch controls for a panel of "antisense" oligodeoxyribonucleotides) also mediated B cell activation and IgM secretion, while the other "controls" had no effect.

Two observations suggested that the mechanism of this B cell activation by the "control" oligodeoxyribonucleotides may not involve antisense effects 1) comparison of vertebrate DNA sequences listed in GenBank showed no greater homology than that seen with non-stimulatory oligodeoxyribonucleotide and 2) the two controls showed no hybridization to Northern blots with 10 μg of spleen poly A+RNA. Resynthesis of these oligodeoxyribonucleotide on a different synthesizer or extensive purification by polyacrylamide gel electrophoresis or high pressure liquid chromatography have identical stimulation, eliminating the possibility of impurity. Similar stimulation was seen using B cells from C3H/HeJ mice, eliminating the possibility that lipopolysaccharide (LPS) contamination could account for the results.

The fact that two "control" oligodeoxyribonucleotide caused B cell activation similar to that of the two "antisense" oligodeoxyribonucleotide raised the possibility that all four oligodeoxyribonucleotide were stimulating B cells through some non-antisense mechanism involving a sequence motif that was absent in all of the other nonstimulatory control oligodeoxyribonucleotide. In comparing these sequences, it was discovered that all of the four stimulatory oligodeoxyribonucleotide contained CpG dinucleotides that were in a different sequence context from the nonstimulatory control.

To determine whether the CpG motif present in the stimulatory oligodeoxyribonucleotide was responsible for the observed stimulation, over 300 oligodeoxyribonucleotide ranging in length from 5 to 42 bases that contained methylated, unmethylated, or no CpG dinucleotides in various sequence contexts were synthesized. These oligodeoxyribonucleotide, including the two original "controls" (ODN 1 and 2) and two originally synthesized as "antisense" (ODN 3D and 3M; Krieg, A. M. *J. Immunol.* 143:2448 (1989)), were then examined for in vitro effects on spleen cells (representative sequences are listed in Table 1). Several oligodeoxyribonucleotides that contained CpG dinucleotides induced B cell activation and IgM secretion; the magnitude of this stimulation typically could be increased by adding more CpG dinucleotides (Table 1; compare ODN 2 to 2a or 3D to 3Da and 3Db). Stimulation did not appear to result from an antisense mechanism or impurity. Oligodeoxyribonucleotides caused no detectable proliferation of γδ or other T cell populations.

Mitogenic oligodeoxyribonucleotide sequences uniformly became nonstimulatory if the CpG dinucleotide was mutated (Table 1; compare ODN 1 to 1a; 3D to 3Dc; 3M to 3Ma; and 4 to 4a) or if the cytosine of the CpG dinucleotide was replaced by 5-methylcytosine (Table 1; ODN 1b, 2b, 3Dd, and 3Mb). Partial methylation of CpG motifs caused a partial loss of stimulatory effect (compare 2a to 2c, Table 1). In contrast methylation of other cytosines did not reduce oligodeoxyribonucleotide activity (ODN 1c, 2d, 3De and 3Mc). These data confirmed that a CpG motif is the essential element present in oligodeoxyribonucleotide that activate B cells.

In the course of these studies, it became clear that the bases flanking the CpG dinucleotide played an important role in determining the murine B cell activation induced by an oligodeoxyribonucleotide. The optimal stimulatory motif was determined to consist of a CpG flanked by two 5' purines (preferably a GpA dinucleotide) and two 3' pyrimidines (preferably a TpT or TpC dinucleotide). Mutations of oligodeoxyribonucleotide to bring the CpG motif closer to this ideal improved stimulation (e.g. Table 1, compare ODN 2 to 2e; 3M to 3Md) while mutations that disturbed the motif reduced stimulation (e.g. Table 1, compare ODN 3D to 3Df; 4 to 4b, 4c and 4d). On the other hand, mutations outside the CpG motif did not reduce stimulation (e.g. Table 1, compare ODN 1 to 1d; 3D to 3Dg; 3M to 3Me). For activation of human cells, the best flanking bases are slightly different (see Table 3).

Of those tested, oligodeoxyribonucleotides shorter than 8 bases were non-stimulatory (e.g. Table 1, ODN 4e). Among the forty-eight 8 base oligodeoxyribonucleotide tested, a highly stimulatory sequence was identified as TCAACGTT (ODN 4) which contains the self complementary "palindrome" AACGTT. In further optimizing this motif, it was found that oligodeoxyribonucleotide containing Gs at both ends showed increased stimulation, particularly if the oligodeoxyribonucleotide were rendered nuclease resistant by phosphorothioate modification of the terminal internucleotide linkages. Oligodeoxyribonucleotide 1585 (5' GGGGT-CAACGTTCAGGGGGG 3') (SEQ ID NO: 47), in which the first two and last five internucleotide linkages are phosphorothioate modified caused an average 25.4 fold increase in mouse spleen cell proliferation compared to an average 3.2 fold increase in proliferation induced by oligodeoxyribonucleotide 1638 (5' AAAATCAACGTTGAAAAAAA 3'), which has the same sequence as ODN 1585 except that the 10 Gs at the two ends are replaced by 10 As. Th effect of the G-rich ends is cis; addition of an oligodeoxyribonucleotide with poly G ends but no CpG motif to cells along with 1638 gave no increased proliferation. For nucleic acid molecules longer than 8 base pairs, non-palindromic motifs containing an unmethylated CpG were found to be more immunostimulatory.

Other octamer oligodeoxyribonucleotide containing a 6 base palindrome with a TpC dinucleotide at the 5' end were also active (e.g. Table 1, ODN 4b, 4c). Other dinucleotides at the 5' end gave reduced stimulation (e.g. ODN 4f; all sixteen possible dinucleotides were tested). The presence of a 3' dinucleotide was insufficient to compensate for the lack of a 5' dinucleotide (e.g. Table 1, ODN 4 g). Disruption of the palindrome eliminated stimulation in octamer oligodeoxyribonucleotide (e.g. Table 1, ODN 4 h), but palindromes were not required in longer oligodeoxyribonucleotide.

The kinetics of lymphocyte activation were investigated using mouse spleen cells. When the cells were pulsed at the same time as oligodeoxyribonucleotide addition and harvested just four hours later, there was already a two-fold increase in $^3$H uridine incorporation. Stimulation peaked at 12–48 hours and then decreased. After 24 hours, no intact oligodeoxyribonucleotide were detected, perhaps accounting for the subsequent fall in stimulation when purified B cells with or without anti-IgM (at a submitogenic dose) were cultured with CpG oligodeoxyribonucleotide, proliferation was found to synergistically increase about 10-fold by the two mitogens in combination after 48 hours. The magnitude of stimulation was concentration dependent and consistently exceeded that of LPS under optimal conditions for both. Oligonucleotides containing a nuclease resistant phosphorothioate backbone were approximately two hundred times more potent than unmodified oligonucleotides.

Cell cycle analysis was used to determine the proportion of B cells activated by CpG-oligodeoxyribonucleotide. CpG-oligodeoxyribonucleotide induced cycling in more than 95% of B cells. Splenic B lymphocytes sorted by flow cytometry into CD23−(marginal zone) and CD23+ (follicular) subpopulations were equally responsive to oligodeoxyribonucleotide-induced stimulation, as were both resting and activated populations of B cells isolated by fractionation over Percoll gradients. These studies demonstrated that CpG-oligodeoxyribonucleotide induce essentially all B cells to enter the cell cycle.

Immunostimulatory Nucleic Acid Molecules Block Murine B Cell Apoptosis

Certain B cell lines, such as WEHI-231, are induced to undergo growth arrest and/or apoptosis in response to crosslinking of their antigen receptor by anti-IgM (Jakway, J. P., et al., "Growth regulation of the B lymphoma cell line WEHI-231 by anti-immunoglobulin, lipopolysaccharide and other bacterial products," *J. Immunol.* 137:2225 (1986); Tsubata, T., J. Wu and T. Honjo: "B-cell apoptosis induced by antigen receptor crosslinking is blocked by a T-cell signal through CD40," *Nature*, 364:634 (1993)). WEHI-231 cells are rescued from this growth arrest by certain stimuli such as LPS and by the CD40 ligand. oligodeoxyribonucleotide containing the CpG motif were also found to protect WEHI-23 1 from anti-IgM induced growth arrest, indicating that accessory cell populations are not required for the effect. Subsequent work indicates that CpG oligodeoxyribonucleotide induce Bcl-x and myc expression, which may account for the protection from apoptosis. Also, CpG nucleic acids have been found to block apoptosis in human cells. This inhibition of apoptosis is important, since it should enhance and prolong immune activation by CpG DNA.

Method for Making Immunostimulatory Nucleic Acids

For use in the instant invention, nucleic acids can be synthesized de novo using any of a number of procedures well known in the art. For example, the B-cyanoethyl phosphoramidite method (S. L. Beaucage and M. H. Caruthers, 1981, Tet. Let. 22:1859); nucleoside H-phosphonate method (Garegg, et al., 1986, *Tet. Let.* 27:4051–4051; Froehler, et al., 1986, *Nucl. Acid. Res.* 14:5399–5407; Garegg, et al., 1986, *Tet. Let.* 27:4055–4058, Gaffney, et al., 1988), *Tet. Let.* 29:2619–2622. These chemistries can be performed by a variety of automated oligonucleotide synthesizers available in the market. Alternatively, oligonucleotides can be prepared from existing nucleic acid sequences (e.g. genomic or cDNA) using known techniques, such as those employing restriction enzymes, exonucleases or endonucleases.

For use in vivo, nucleic acids are preferably relatively resistant to degradation (e.g. via endo- and exo-nucleases). Secondary structures, such as stem loops, can stabilize nucleic acids against degradation. Alternatively, nucleic acid stabilization can be accomplished via phosphate backbone modifications. A preferred stabilized nucleic acid can be accomplished via phosphate backbone modifications. A preferred stabilized nucleic acid has at least a partial phosphorothioate modified backbone. Phosphorothioates may be synthesized using automated techniques employing either phosphoramidate or H-phosphonate chemistries. Aryl- and alkyl-phosphonates can be made for example as described in U.S. Pat. No. 4,469,863; and alkylphosphotriesters (in which the charged oxygen moiety is alkylated as described in U.S. Pat. No. 5,023,243 and European Patent No. 092, 574) can be prepared by automated solid phase synthesis using commercially available reagents. Methods for making other DNA backbone modifications and substitutions have been described (Uhlmann, E. and Peyman, A., 1990, *Chem Rev.* 90:544; Goodchild, J., 1990, *Bioconjugate Chem.* 1:165). 2'-O-methyl nucleic acids with CpG motifs also cause immune activation, as do ethoxy-modified CpG nucleic acids. In fact, no backbone modifications have been found that completely abolish the CpG effect, although it is greatly reduced by replacing the C with a 5-methyl C.

For administration in vivo, nucleic acids may be associated with a molecule that results in higher affinity binding to target cell (e.g. dendritic cell) surfaces and/or increased cellular uptake by target cells to form a "nucleic acid delivery complex." Nucleic acids can be ionically, or covalently associated with appropriate molecules using techniques which are well known in the art. A variety of coupling or crosslinking agents can be used, for example protein A, carbodiimide, and N-succinimidyl-3-(2-pyridyldithio) propionate (SPDP). Nucleic acids can alternatively be encapsulated in liposomes or virosomes using well-known techniques.

Theraneutic Uses ofimmunostimulatory Nucleic Acid Molecules

Based on their immunostimulatory properties, nucleic acid molecules containing at least one unmethylated CpG dinucleotide can be used as described in detail. The nucleic acid molecules may also be used as set forth herein and in Co-pending parent patent application U.S. Ser. No. 08/960, 774.

Immunostimulatory nucleic acid molecules can also be administered to a subject in conjunction with a vaccine to boost a subject's immune system and thereby effect a better response from the vaccine. Preferably the immunostimulatory nucleic acid molecule is administered slightly before or at the same time as the vaccine. A conventional adjuvant may optionally be administered in conjunction with the vaccine, which is minimally comprised of an antigen, as the conventional adjuvant may further improve the vaccination by enhancing antigen absorption.

When the vaccine is a DNA vaccine at least two components determine its efficacy. First, the antigen encoded by the vaccine determines the specificity of the immune response. Second, if the backbone of the plasmid contains CpG motifs, it functions as an adjuvant for the vaccine. Thus, CpG DNA acts as an effective "danger signal" and causes the immune system to respond vigorously to new antigens in the area. This mode of action presumably results primarily from the stimulatory local effects of CpG DNA on dendritic cells and other "professional" antigen presenting cells, as well as from the co-stimulatory effects on B cells.

Immunostimulatory oligonucleotides and unmethylated CpG containing vaccines, which directly activate lymphocytes and co-stimulate an antigen-specific response, are fundamentally different from conventional adjuvants (e.g. aluminum precipitates), which are inert when injected alone and are thought to work through absorbing the antigen and thereby presenting it more effectively to immune cells. Further, conventional adjuvants only work for certain antigens, only induce an antibody (humoral) immune response (Th2), and are very poor at inducing cellular immune responses (Th1). For many pathogens, the humoral response contributes little to protection, and can even be detrimental.

In addition, an immunostimulatory oligonucleotide can be administered prior to, along with or after administration of a chemotherapy or immunotherapy to increase the responsiveness of the malignant cells to subsequent chemotherapy or immunotherapy or to speed the recovery of the bone marrow through induction of restorative cytokines such as GM-CSF. CpG nucleic acids also increase natural killer cell lytic activity and antibody dependent cellular cytotoxicity (ADCC). Induction of NK activity and ADCC may likewise be beneficial in cancer immunotherapy, alone or in conjunction with other treatments.

Another use of the described immunostimulatory nucleic acid molecules is in desensitization therapy for allergies, which are generally caused by IgE antibody generation against harmless allergens. The cytokines that are induced by unmethylated CpG nucleic acids are predominantly of a class called "Th1" which is most marked by a cellular immune response and is associated with IL-12 and IFN-γ. The other major type of immune response is termed as Th2 immune response, which is associated with more of an antibody immune response and with the production of IL-4, IL-5 and IL-10. In general, it appears that allergic diseases are mediated by Th2 type immune responses and autoimmune diseases by Th1 immune response. Based on the ability of the immunostimulatory nucleic acid molecules to shift the immune response in a subject from a Th2 (which is associated with production of IgE antibodies and allergy) to a Th1 response (which is protective against allergic reactions), an effective dose of an immunostimulatory nucleic acid (or a vector containing a nucleic acid) alone or in conjunction with an allergen can be administered to a subject to treat or prevent an allergy.

Nucleic acids containing unmethylated CpG motifs may also have significant therapeutic utility in the treatment of asthma. Th2 cytokines, especially IL-4 and IL-5 are elevated in the airways of asthmatic subjects. These cytokines, especially IL-4 and IL-5 are elevated in the airways of asthmatic subjects. These cytokines promote important aspects of the asthmatic inflammatory response, including IgE isotype switching, eosinophil chemotaxis and activation and mast cell growth. Th1 cytokines, especially IFN-γ and IL-12, can suppress the formation of Th2 clones and production of Th2 cytokines.

As described in Co-pending parent patent application U.S. Ser. No. 08/960,774, oligonucleotides containing an unmethylated CpG motif (i.e. TCCATGACGTTCCTGACGTT; SEQ IN NO: 97), but not a control oligonucleotide (TCCATGAGCTTCCTGAGTCT; SEQ ID NO: 98) prevented the development of an inflammatory cellular infiltrate and eosinophilia in a murine model of asthma. Furthermore, the suppression of eosinophilic inflammation was associated with a suppression of Th2 response and induction of a Th1 response.

For use in therapy, an effective amount of an appropriate immunostimulatory nucleic acid molecule alone or formulated as a delivery complex can be administered to a subject by any mode allowing the oligonucleotide to be taken up by the appropriate target cells (e.g. dendritic cells). Preferred routes of administration include oral and transdermal (e.g. via a patch). Examples of other routes of administration include injection (subcutaneous, intravenous, parenteral, intraperitoneal, intrathecal, etc.). The injection can be in a bolus or a continuous infusion.

A nucleic acid alone or as a nucleic acid delivery complex can be administered in conjunction with a pharmaceutically acceptable carrier. As used herein, the phrase "pharmaceutically acceptable carrier" is intended to include substances that can be coadministered with a nucleic acid or a nucleic acid delivery complex and allows the nucleic acid to perform its indicated function. Examples of such carriers include solutions, solvents, dispersion media, delay agents, emulsions and the like. The use of such media for pharmaceutically active substances are well known in the art. Any other conventional carrier suitable for use with the nucleic acids fall within the scope of the instant invention.

The term "effective amount" of a nucleic acid molecule refers to the amount necessary or sufficient to realize a desired biologic effect. For example, an effective amount of a nucleic acid containing at least one unmethylated CpG for treating an immune system deficiency could be that amount necessary to eliminate a tumor, cancer, or bacterial, viral or fungal infection. An effective amount for use as a vaccine adjuvant could be that amount useful for boosting a subject's immune response to a vaccine. An "effective amount" for treating asthma can be that amount useful for redirecting a Th2 type of immune response that is associated with asthma to a Th1 type of response. The effective amount for any particular application can vary depending on such factors as the disease or condition being treated, the particular nucleic acid being administered (e.g. the number of unmethylated CpG motifs or their location in the nucleic acid), the size of the subject, or the severity of the disease or condition. One of ordinary skill in the art can empirically determine the effective amount of a particular oligonucleotide without necessitating undue experimentation.

The compositions of the invention, including activated dendritic cells, isolated CpG nucleic acid molecules, cytokines, and mixtures thereof are administered in pharmaceutically acceptable compositions. The compositions may be administered by bolus injection, continuous infusion, sustained release from implants, aerosol, or any other suitable technique known in the art.

It is also contemplated according to the methods of the invention that any compositions of the invention may also be administered in conjunction with other immune stimulating agents, such as for instance cytokines. Cytokines, include but are not limited to, IL-1, IL-2, IL-4, IL-5, IL-6, IL-7, IL-10, IL-12, IL-1 5, granulocyte-macrophage colony stimulating factor (G-MCSF), granulocyte colony stimulating factor (GCSF), interferon-y (IFN-γ), tumor necrosis factor (TNF), TGF-β, FLT-3 ligand, and CD40 ligand.

As reported herein, in response to unmethylated CpG containing nucleic acid molecules, an increased number of spleen cells secrete IL-6, IL-12, IFN-γ, IFN-α, IFN-β, IL-1, IL-3, IL-10, TNF-α, TNF-β, GM-CSF, RANTES, and probably others. The increased IL-6 expression was found to occur in B cells, CD4+T cells, monocytic cells, as well as dendritic cells.

FLT3 ligand is a class of compounds described in EP0627487A2 and W094/28391. A human FLT3 ligand cDNA was deposited with the American Tissue Type Culture Collection, Rockville, Md., and assigned accession number ATCC 69382. Interleukins have been described extensively in the art, e.g., Mosley, et al., 1989, *Cell*, 59:335, Idzerda, et al., 1990, *J. Exp. Med*, 171:861. GM-CSF is commercially available as Sargramostion. Leukine (Immunex).

Systemic administration of CpG alone in some embodiments is useful for immunotherapy against antigens. Alternative agents like GM-CSF have a shorter half life, although their synergistic effects with CpG will likely make this combination useful. On the other hand, some activators of dendritic cells like LPS or inflammatory cytokines (TNF) have dose limiting toxicity, which makes their systemic use for this purpose not practical. The present study provides the functional rationale and methods for the use of CpG for dendritic cell-based immunotherapeutic strategies against cancer and for its use as an adjuvant in humans.

Systemically administered CpG oligonucleotides enhances the availability of immature and mature dendritic cells in the blood and in tissues.

The invention is also useful for in vitro screening assays. For instance, immature dendritic cells may be used in vitro to identify other CpG specific motifs which are useful for activating or causing maturation of dendritic cells. These motifs may then be used in vivo or ex vivo for activating dendritic cells. Additionally, the same type of assay may be used to identify cytokines or other immunostimulatory molecules which may have synergistic adjuvant effects when combined with isolated CpG nucleic acid sequences of the invention.

Another assay useful according to the invention is an assay for identifying compounds which inhibit dendritic cell activation or maturation. The assay would involve the addition of a putative drug to a immature dendritic cell which is activated by CpG. If the putative drug prevents activation, then it may be a compound which is therapeutically capable of inhibiting activation or maturation of the dendritic cell. Such compounds would be useful in methods of gene therapy when it is desirable to specifically inhibit the immune response to prevent an immune response against the therapeutic protein. For instance, when Factor VIII is delivered by gene therapy methods, it is desirable to prevent an immune response from developing against the therapeutic Factor VIII. It is also useful for preventing immune response to transplanted heterologous tissue.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Example 1

Generation and Characterization of Dendritic Cells

Methods

Isolation of dendritic cells: Dendritic cells represent a small population of peripheral blood mononuclear cells (0.1 to 0.4 %). They express substantial levels of CD4, but lack the T cell molecules CD3, CD8, and T cell receptor, and other lineage markers (CD19, CD14, CD16, CD56) (O'Doherty U, et al., "Dendritic cells freshly isolated from human blood express CD4 and mature into typical immunostimulatory dendritic cells after culture in monocyte-conditioned medium", *J Exp Med*, 1993; 178: 1067–1076). Using these characteristics, dendritic cells can be separated by high gradient immunomagnetic cell sorting using the VARIOMACS technique (Miltenyi Biotec Inc., Auburn, Calif.). Peripheral blood mononuclear cells were obtained from buffy coats of healthy blood donors (Elmer L. DeGowin Blood Center, University of Iowa) by Ficoll-Paque density gradient centrifugation (Histopaque-1077, Sigma Chemical Co., St. Louis, Mo.) as described (Hartmann G, et al., "Specific suppression of human tumor necrosis factor-alpha synthesis by antisense oligodeoxynucleotides", *Antisense Nucleic Acid Drug Dev*, 1996; 6: 291–299). Cells were resuspended in phosphate buffered saline (0.5 % bovine serum albumin, 2 mM EDTA, pH 7.4) and incubated with colloidal superparamagnetic microbeads conjugated with CD3, CD14, CD16, CD19 and CD56). Thereafter cells were passed over a depletion column in a strong magnetic field. Cells in the flow through were collected, washed two times, incubated with a microbead-conjugated antibody to CD4, and passed over a positive selection column. CD4-positive cells were eluted from the column by removal of the column from the magnetic device. Eluted cells were passed over a second column to enhance purity of the preparation. By this technique we were able to isolate $6 \times 10^5$ to $2.2 \times 10^7$ dendritic cells from $2 \times 10^8$ to $5 \times 10^8$ peripheral blood mononuclear cells in a purity of 94 to 99 % (MHC class II expression, lineage marker negative). Viability was determined by trypan blue exclusion (>95 %). In light microscopy, purified cells had the appearance of medium sized lymphocytes.

Cell culture Cells were suspended in RPMI 1640 culture medium supplemented with 10 % (v/v) heat-inactivated (56° C., 1 h) FCS (HyClone, Logan, Utha), 1.5 mM L-glutamine, 100 U/ml penicillin and 100 μg/ml streptomycin (all from Gibco BRL, Grand Island, N.Y.) (complete medium). All compounds were purchased endotoxin-tested. Freshly prepared dendritic cells (final concentration $4 \times 10^5$ cells/ml) were cultured in 96-well plates in 200 μl complete medium in a 5% $CO_2$ humidified incubator at 37° C. for either 48 hours or 72 hours as indicated. The cell culture medium contained 800 U/ml GMCSF ($1.25 \times 10^4$ U/mg; Genzyme, Cambridge, Mass.), 10 ng/ml LPS (from salmonella typhimurium, Sigma Chemical Co., St. Louis, Mo.) or oligonucleotides as indicated.

Results

Figure 8:
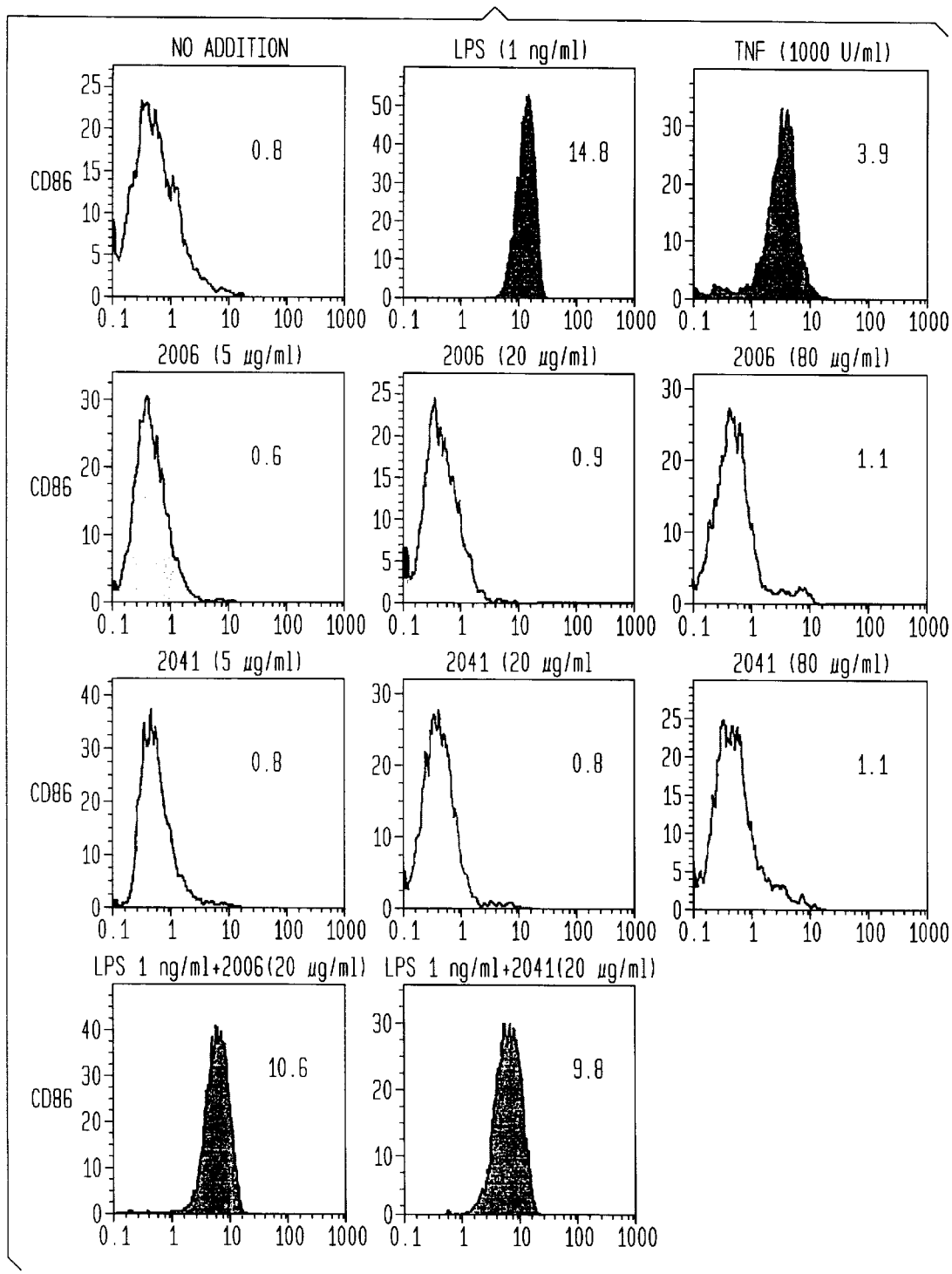
FIG. 8 shows FACS charts demonstrating that CD86 expression on monocyte-derived Dendritic cells is induced by LPS but not by CpG. CD14-positive monocytes were prepared from PBMC by immunomagnetic separation and incubated in the presence of GMCSF (800 U/ml) and IL-4 (500 U/ml, Genzyme, Cambridge, Mass.). After five days (fresh medium and cytokines added every other day), cells showed the characteristic surface marker pattern of monocyte-derived dendritic cells (lineage marker negative, MHC II bright, CD1a bright, CD40 intermediate, CD54 intermediate, CD80 dim, CD86 dim) and characteristic morphology. From day 5 to day 7, LPS (1 ng/ml), TNF (1000 U/ml) or oligonucleotides in the indicated concentrations were added. CD 86 expression is measured by flow cytometry (numbers represent mean fluorescence intensity). In this series of experiments, the non-CpG phosphorothioate control oligonucleotide 2041 (5'-CTG GTC TTT CTG GTT TTT TTC TGG-3') (SEQ ID NO: 93) was used. The results are representative for 8 independent experiments, in which CpG did not stimulate monocyte-derived dendritic cells.

Dendritic cells can be obtained in large numbers by incubation of CD14-positive monocytes with GMCSF and IL-4 for 7 days. However, upon withdrawal of IL-4 these cells lose their dendritic cell characteristics and become CD14 positive macrophages (Hausser G, et al. "Monocyte-derived dendritic cells represent a transient stage of differentiation in the myeloid lineage", *Immunobiology*, 1997; 197: 534–542). In addition, IL-4 induces a Th2 immune response which may not be optimal for the induction of a specific cytotoxic T-cell response. Therefore, monocyte-derived dendritic cells, despite their availability in large numbers, may not be optimal for immunotherapeutic purposes. We found that monocyte-derived dendritic cells are sensitive to LPS but surprisingly are not activated by CpG motifs (FIG. 8). It is believed that the inability of monocyte-derived DC to respond to CpG might be due to the unphysiologic methods by which these cells are prepared. Consequently, the effect of CpG oligonucleotides on primary peripheral blood DC was examined.

Physiologically, DC are present in small numbers (<0.5%) in peripheral blood mononuclear cells. Blood dendritic cells can be identified by the expression of CD4 and HLA-DR surface antigens and the absence of lineage markers (B cell, T cell, NK cell and monocyte). Immunomagnetic depletion of lineage-positive cells and subsequent positive selection of CD4-positive cells allows the isolation of DC from peripheral blood. In our experiments, we obtained 0.7 to $2.4 \times 10^6$ DC from single buffy coats (2.5 to $5 \times 10^8$ mononuclear cells). The purity of the DC preparation (MHC II bright, lineage marker negative) varied from 93% to 99%. Freshly isolated dendritic cells have the appearance of medium sized lymphocytes. During a two days incubation with GMCSF, the cells gain the specific characteristics of dendritic cells. Morphologically, they enlarge and exhibit sheet like cell processes. They express low levels of the co-stimulatory molecules CD54 (ICAM-1, adhesion molecule), CD80 (B7-1), CD86 (B7-2) and CD40. Flow cytometric characteristics of dendritic cells after two days of culture with GMCSF are depicted in table 1.

Example 2

CpG Substitutes for GMCSF for DC Survival

Methods

Oligodeoxynucleotides Unmodified (phosphodiester) and modified nuclease-resistant (phosphorothioate) oligodeoxyribonucleotide were purchased from Operon Technologies (Alameda, Calif.). The optimal motif recognized by human immune cells is different from the optimal mouse motif. Based on other studies in which we tested a large number of oligonucleotides for their ability to activate human B-cells and NK-cells, we selected particularly potent oligonucleotides as examples of a family of active CpG-containing oligonucleotides for the use in the present study. The CpG oligonucleotides used were: 2006 (24-mer), 5'-TCG TCG TTT TGT CGT TTT GTC GTT-3' (SEQ ID NO: 84), completely phosphorothioate-modified, and 2080 (20-mer), 5'-TCG TCG TTC CCC CCC CCC CC-3' (SEQ ID NO: 94), un-modified phosphodiester. The non-CpG control oligonucleotides used were: 2117 (24-mer), 5'-TQG TQG TTT TGT QGT TTT GTQ GTT-3' (SEQ ID NO: 95), Q=5 methyl cytosine, completely phosphorothioate-modified, and 2078 (20-mer), 5'-TGC TGC TTC CCC CCC CCC CC-3' (SEQ ID NO: 96), unmodified phosphodiester. Oligonucleotides were diluted in TE (10 mM Tris-HCl, 1 mM EDTA, pH 8) using pyrogen-free reagents. Phosphorothioate oligonucleotides (2006 and 2117) were added at a final concentration of either 2 µg/ml or 6 µg/ml as indicated. Based on preliminary experiments in which no effect was seen after a single addition, phosphodiester oligonucleotides were added at 0 hours, 12 hours and 24 hours at 30 µg/ml each (total addition 90 µg/ml).

Flow cytometry Flow cytometric data on 2500 viable cells per sample or 4000 total counts were acquired on a FACScan (Beckton Dickinson Immunocytometry systems, San Jose, Calif.). Spectral overlap was corrected by appropriate compensation. Fluorescence detector settings were identical in all experiments. Analysis was performed on viable dendritic cells present within a morphologic gate (FSC, SSC, >94% of cells MHC II positive and lineage marker negative). Data were analyzed using the computer program FlowJo (version 2.5.1, Tree Star, Inc., Stanford, Calif.).

Results

The presence of GMCSF is required for the survival of freshly isolated DC from peripheral blood. In the absence of GMCSF, DC undergo apoptosis during the first two days of cell culture. We examined the effect of CpG oligonucleotides on survival of DC in cell culture. Freshly isolated DC were incubated in the presence of GMCSF or oligonucleotides for 48 hours. Light microscopy showed the formation of cell clusters within one day for both the sample with GMCSF alone and the sample with the CpG phosphorothioate oligonucleotide 2006. While the size of the clusters was not different between these two samples, the DC incubated with 2006 displayed longer processes seen at the surface of the clusters, resembling the morphology of mature dendritic cells. This difference was distinctive between GMCSF and 2006 samples by using light microscopy. Without GMCSF or CpG, no clusters could be found but there was an increasing number of non-viable cells as revealed by trypan blue staining. Viability of DC was quantified by flow cytometry (FIG. 1). Cell survival was dramatically improved in the presence of CpG motifs. This effect was found to be CpG specific for both phosphorothioate (2006, 2117) and phosphodiester (2080, 2078) oligonucleotides, since both non-CpG control oligonucleotides (2117: methylated version of 2006; 2078: CpGs in 2080 inverted to GpCs) showed no improved survival compared to the sample with cells only. While for the nuclease resistant phosphorothioate oligonucleotides a single addition of 2 µg/ml was sufficient, the phosphodiester oligonucleotides were added repeatedly in a higher concentration (30 µg/ml at 0 hours, 12 hours ard 24 hours).

Figure 2:
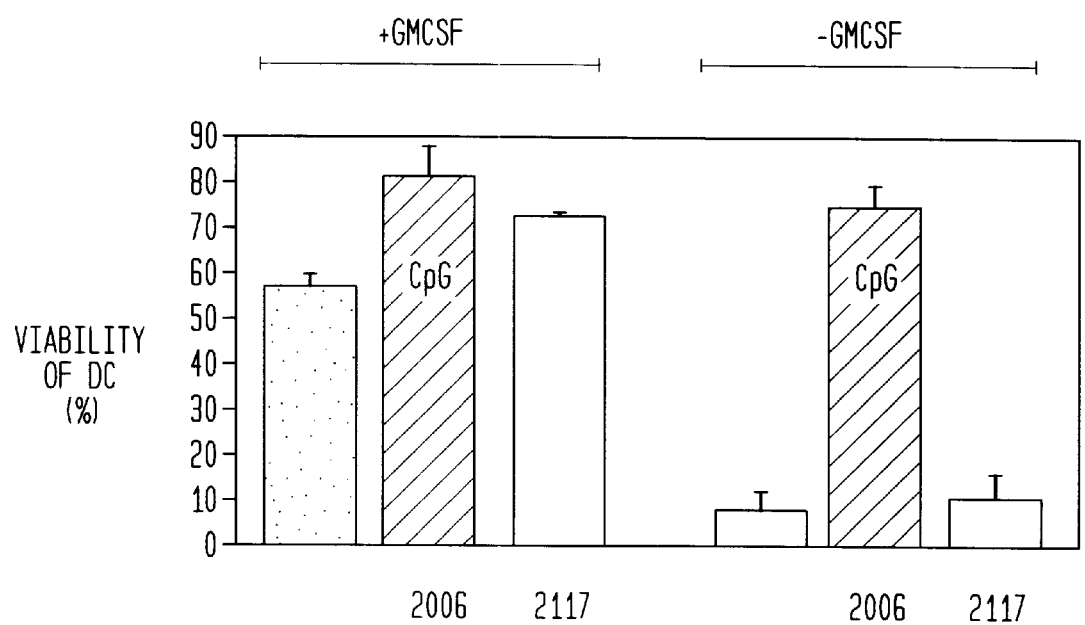
FIG. 2 is a graph showing that the combination of CpG and GMCSF enhances viability of dendritic cells. Dendritic precursor cells were isolated from peripheral blood and incubated for 48 hours with GMCSF (800 U/ml) and oligonucleotides (2006: CpG phosphorothioate; 2117: CpGs in 2006 methylated; 2 μg/ml) as indicated. Viability was examined by flow cytometry. Data represent the mean of two independent experiments.

Quantification of viability (percentage of viable cells of all counted events in flow cytometry) revealed that a single addition of 2006 (2 µg/ml) to freshly prepared DC was superior to GMCSF (800 U/ml) in promoting cell survival (74.3+−5.2% vs. 57.1+−2.3%) (FIG. 2). The ccmbination of GMCSF and 2006 further increased the number of viable cells (81.0+−6.7%). In the presence of the control oligonucleotide 2117 (2 µg/ml) cell survival was low and ccmparable to the sample with cells only (10.8+−5.2% and 7.4+−4.2%). These results show that CpG can substitute for GMCSF for promoting DC survival, and that the combination of both is favorable over each of them alone.

Example 3

Increased Size and Granularity of DC Induced by CpG is Associated with Enhanced Expression of MHC II Methods Surface antigen staining At the indicated time points, cells were harvested and surface antigen staining was performed as previously described. Monoclonal antibodies to HLA-DR (Immu-357), CD80 (MAB104) and to CD83 (HB15A) were purchased from Immunotech, Marseille, France. All other antibodies were purchased from Pharmingen, San Diego, Calif.: mABs tc CD1a (HI149), CD3 (UCHT1), CD14 (M5E2), CD19 (B43), CD40 (5C3), CD54 (HA58), CD86

(2331 (FUN-1)). FITC-labeled IgG$_1$,κ (MOPC-21) and PE-labeled IgG$_{2b}$,κ (27–35) were used to control for specific staining.

Results

Figure 3:
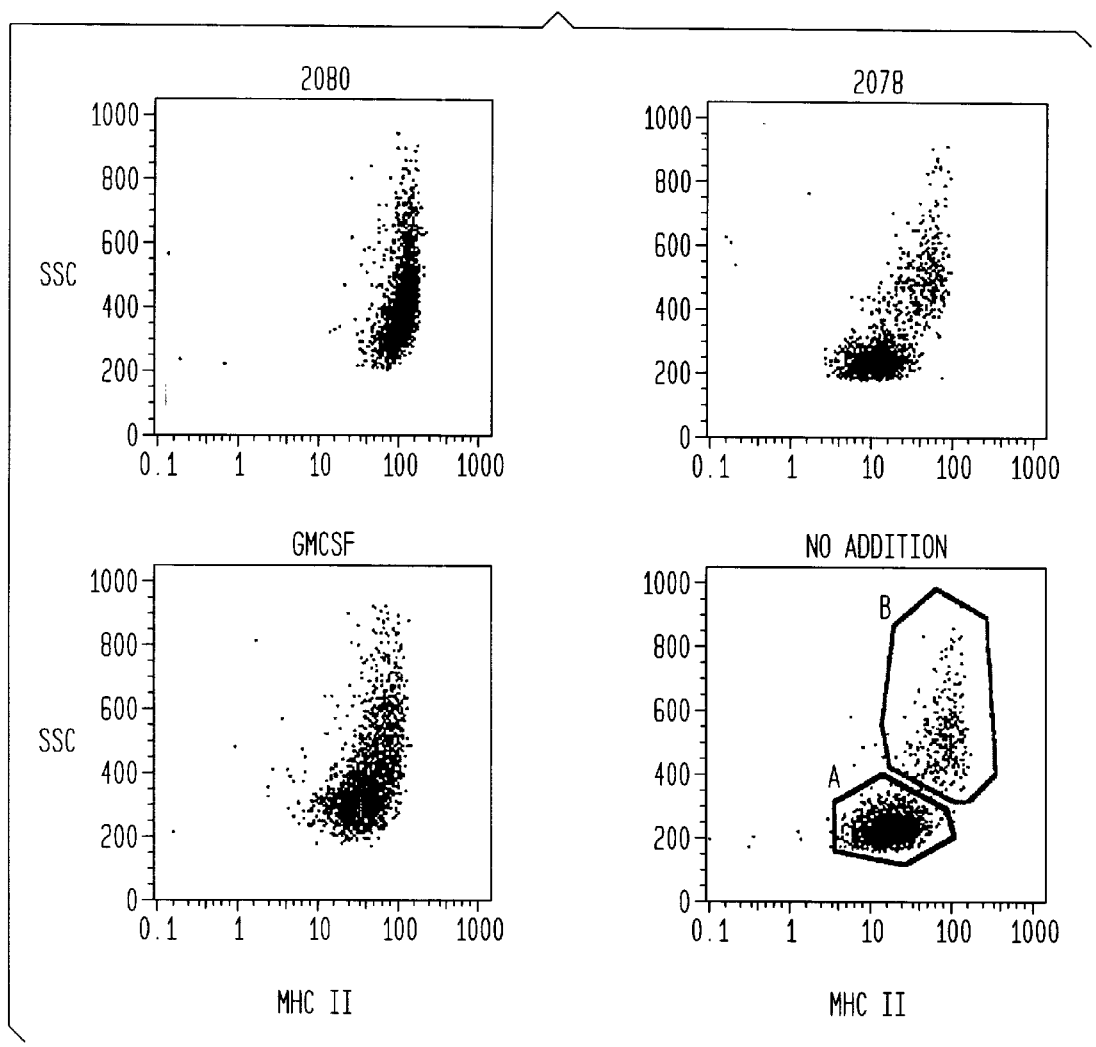
FIG. 3 shows FACS charts demonstrating that an increase in dendritic cell size is associated with enhanced MHC II expression. Dendritic precursor cells are incubated for 48 hours in the presence of GMCSF (800 U/ml) and oligonucleotides as indicated and examined by flow cytometry (sideward scatter, SSC). Viable cells (2500 per sample) were counted. Phosphodiester oligonucleotides (2080: CpG; 2078: non-CpG) were added at 0 hours, 12 hours and 24 hours (30 μg/ml each time point).

Flow cytometric analysis suggested that differentiation of DC is enhanced by CpG and is associated with an increase of cell size (FSC) and granularity (SSC) (FIG. 1). The surface expression of MHC II is known to be positively correlated with differentiation of DC. DC isolated from peripheral blood were cultured in the presence of GMCSF and oligonucleotides for 48 hours, stained for HLA-DR (MHC II) and examined by flow cytometry (2500 viable cells counted) (FIG. 3). In the sample with cells only or the non-CpG oligonucleotide (2078), a large immature population with low granularity (SSC) and lower MHC II expression was found (FIG. 3 region A). A small population showed high SSC and high expression of MHC II representing differentiated DC (FIG. 3, region B). The addition of either GMCSF or the CpG oligonucleotide 2080 enhanced both granularity and MHC II expression on a per cell basis (FIG. 3 left two panels). The CpG oligonucleotide 2080 showed a superior effect compared to GMCSF indicating that CpG promotes differentiation of DC in addition to an enhancement of cell survival.

Example 4

CpG Increases Co-stimulatory Molecules on DC

Methods

Detection of endotoxin The activity of LPS is standardized by the FDA using the limulus amebocyte lysate (LAL) assay (EU/ml). The lower detection limit of the LAL-assay in our hands was 0.03 EU/ml (LAL-assay Bio Whittaker, Walkersville, Md.). The LPS sample used in our studies (from salmonella typhimurium, Sigma Chemical Co., St. Louis, Mo.) had an activity of 4.35 ng/EU. No endotoxin could be detected in the oligonucleotides (<0.075 EU/mg).

Results

Figure 4:
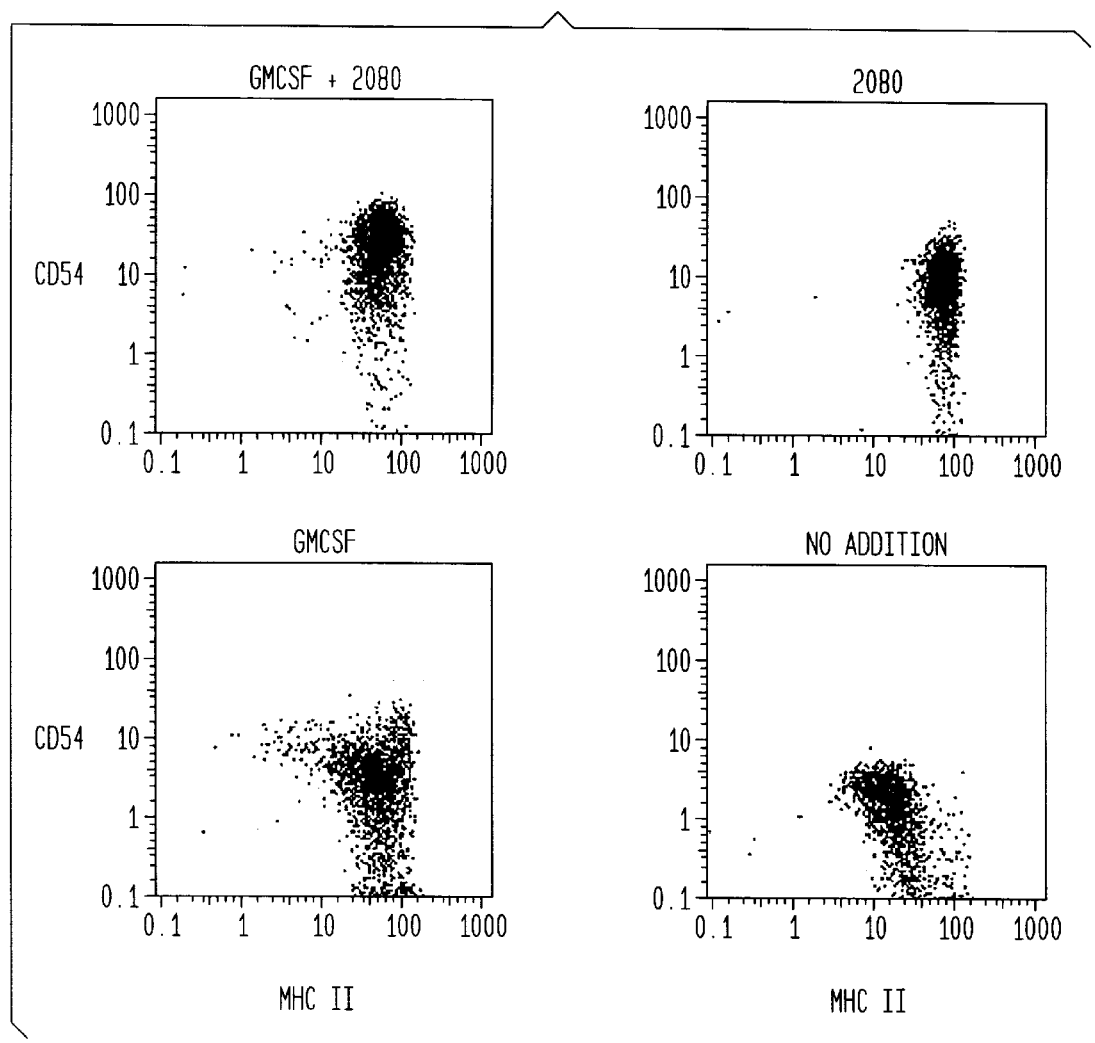
FIG. 4 shows FACS charts demonstrating that ICAM-1 and MHC II expression of dendritic cells in response to GMCSF and CpG. Dendritic precursor cells were incubated for 48 hours in the presence of GMCSF (800 U/ml) and 2006 (CpG phosphorothioate; 6 μg/ml). Expression of ICAM-1 (CD54) and MHC II was examined by flow cytometry (2500 viable cells are counted in each sample).
Figure 5A:
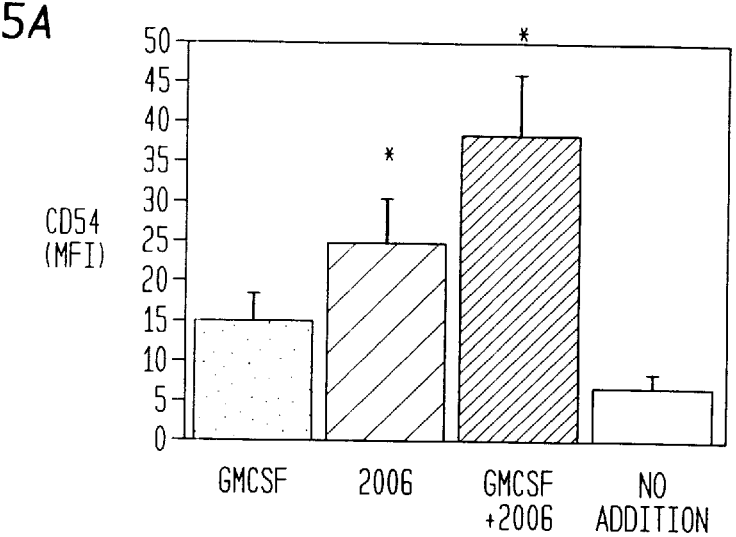
FIG. 5 is graphs depicting induction of co-stimulatory molecule expression on dendritic cells by CpG. Dendritic precursor cells were incubated for 48 hours in the presence of GMCSF (800 U/ml) and oligonucleotides (2006: CpG phosphorothioate, 6 μg/ml) as indicated. Expression of CD54 (ICAM-1) (panel A), CD86 (B7-2) (panel B) and CD40 (panel C) was quantified by flow cytometry (MFI, mean fluorescence intensity). The combination of GMCSF and 2006 shows synergy for increasing the expression of CD86 and CD40, while the effect on CD54 was additive. Results represent the mean of 5 independent experiments (CD54 and CD86) and 4 experiments (CD40). Statistical significance of the increase compared to the cell only sample is indicated by * ($p<0.05$). Statistical evaluation is performed by the unpaired t-test, error bars indicate SEM.
Figure 5B:
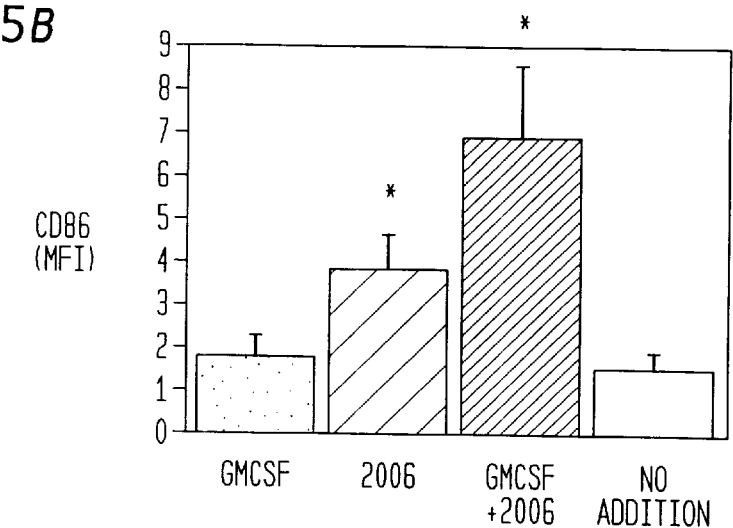
Figure 5C:
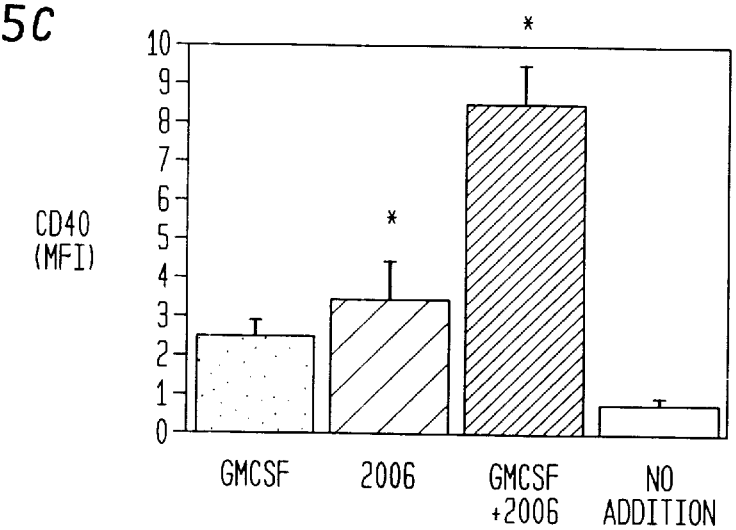

Differentiation of DC by the criteria of morphology and MHC II expression is not sufficient for the induction of a specific immune response by DC. Functional activation of DC requires by the expression of co-stimulatory molecules. We examined the effect of CpG on the expression of the intercellular adhesion molecule-1 (ICAM-1, CD54), and the co-stimulatory surface molecules B7-2 (CD86) and CD40. First, we were interested if an enhanced expression of MHC II on DC (differentiation) was correlated to activation reflected by CD54 expression. No positive correlation could be found confirming that differentiation is not necessarily associated with activation of DC (FIG. 4). The expression of the co-stimulatory molecules CD54 (FIG. 5, panel A), CD86 (FIG. 5, panel B) and CD40 (FIG. 5, panel C) was quantified in flow cytometry by the mean fluorescence intensity (MFI) of viable DC. In all experiments, CpG was superior to GMCSF in enhancing expression of co-stimulatory molecules. Compared to the cells only sample, the CpG oligonucleotide 2006 enhanced the expression of CD54 (25.0+−5.7 vs. 7.0+−1.8; p=0.02, n=5), CD86(3.9+−0.8 vs. 1.6+−0.3; p=0.01; n=5) and CD40 (3.5+−1.0 vs. 0.9+−0.1; p=0.04, n=4). The combination of GMCSF and 2006 showed an additive effect for CD54 (38.5+−7.9; p=0.03; n=5), and enhanced the expression of CD86 and CD40 synergistically (CD86: 7.0+−1.6; p=0.01; n=5; CD40: 8.5+−1.0; p<0.01; n=4).

Figure 6A:
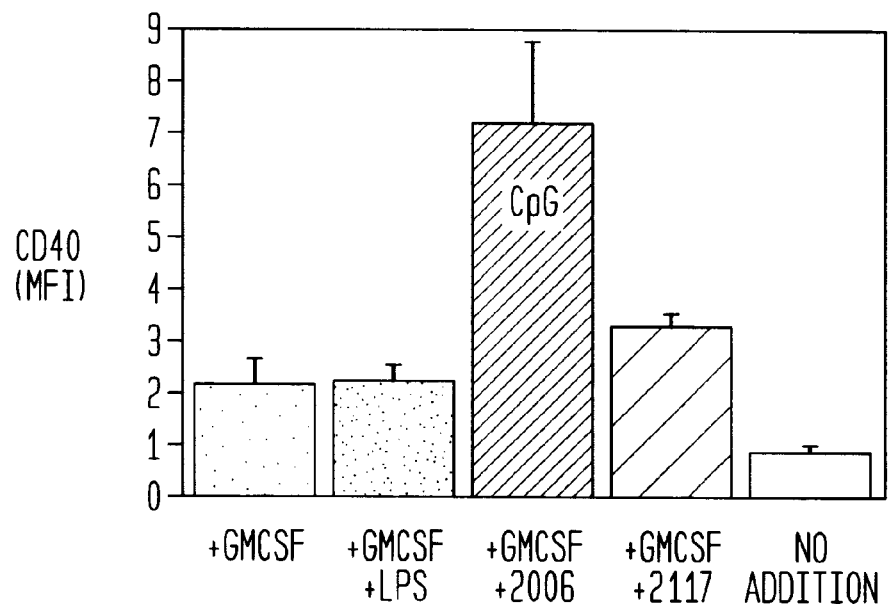
FIG. 6 is graphs depicting the enhancement of CD40 expression on dendritic cells is CpG specific and not induced by LPS. Dendritic precursor cells are cultured for 48 hours in the presence of GMCSF (800 U/ml), LPS (10 ng/ml) and oligonucleotides (2006, CpG phosphorothioate, 6 μg/ml: 2117, methylated 2006; 2080 CpG phosphodiester, 30 μg/ml at 0 hours, 12 hours and 24 hours; 2078 GpC version of 2080). CD40 expression is examined by flow cytometry (MFI, mean fluorescence intensity). Panel A and panel B show the results of two separate sets of experiments. Panel A shows CpG specificity (methylated control oligonucleotide) for the synergy of CpG and GMCSF for induction of CD40 expression. Panel B shows that CpG is equally effective in enhancing CD40 expression as GMCSF, and that this effect is CpG specific (GpC control oligonucleotide). Panel A and B represent the mean of two independent experiments each.
Figure 6B:
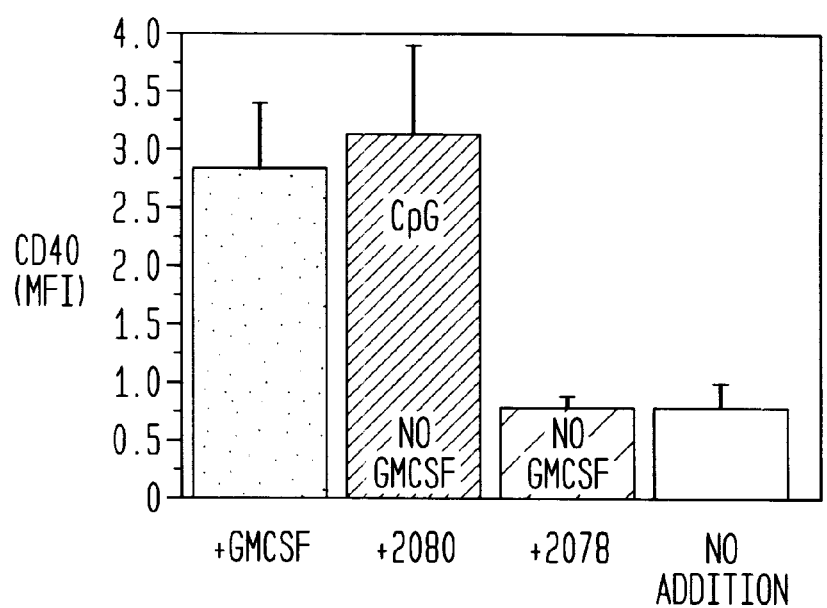

Specificity was tested using 2117 (methylated version of 2006) and 2078 (GpC version of 2080). As shown in FIG. 6 for CD40, the non-CpG oligonucleotide 2117 showed no synergistic enhancement of CD40 expression when combined with GMCSF (FIG. 6 panel A). The non-CpG oligonucleotide 2078 alone did not induce CD40 compared to cells only (FIG. 6 B). Induction of CD86 (FIG. 7 panel A) and CD54 (FIG. 7 panel B) was also found to be CpG specific.

Figure 7A:
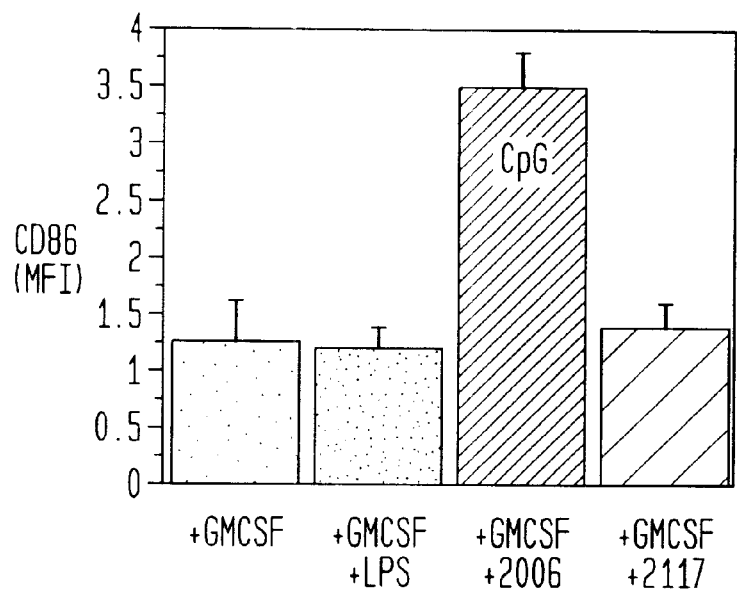
FIG. 7 is graphs depicting the induction of CD54 and CD86 expression on dendritic cells is CpG specific and not induced by LPS. Dendritic precursor cells are cultured for 48 hours in the presence of GMCSF (800 U/ml), LPS (10 ng/ml) and oligonucleotides (2006, CpG phosphorothioate, 2 μg/ml: 2117, methylated 2006). CD54 (panel A) and CD86 (panel B) expression is examined by flow cytometry (MFI, mean fluorescence intensity). Panel A and B represent the mean of two independent experiments (error bars indicate SEM).
Figure 7B:
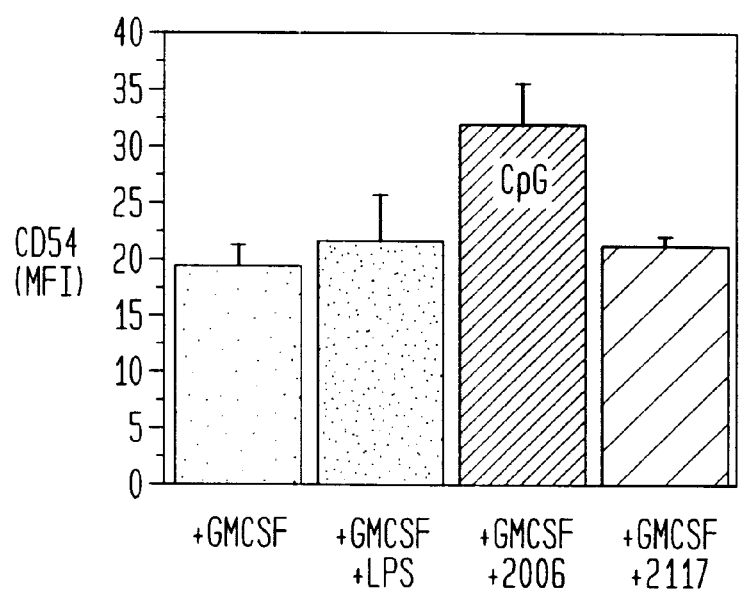

Interestingly, LPS (10 ng/ml) showed no or only slight activation of DC isolated from peripheral blood (FIG. 6 and FIG. 7). This is surprising, since a ten-fold less concentration of LPS (1 ng/ml) stimulates human CD14-positive monocytes to express CD54 and CD86, and to produce the proinflammatory cytokines TNF and IL-6. TNF synthesis of monocytes can be found for LPS concentrations as low as 10 pg/ml, and 1 ng/ml already induces the maximal response in terms of cytokine production. Monocyte-derived DC are highly sensitive to LPS but do not respond to CpG suggesting major functional differences between monocyte-derived DC and DC isolated from peripheral blood (FIG. 8).

Example 5

CpG Induces Maturation (CD83 expression) of DC

Results

Figure 9:
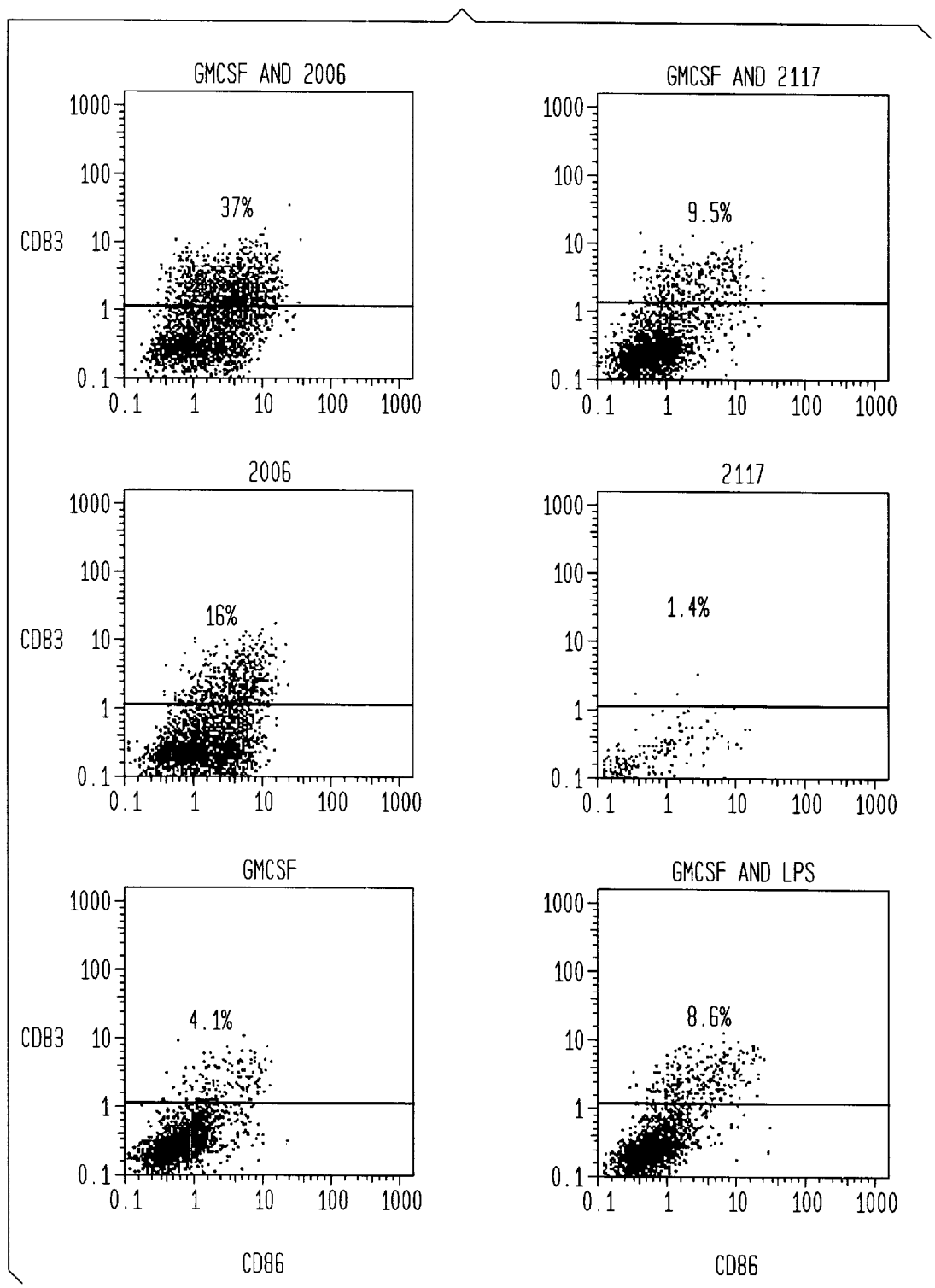
FIG. 9 shows FACS charts demonstrating that CpG induces maturation (CD83 expression) of dendritic cells. After 48 hours incubation with GMCSF (800 U/ml), LPS (10 ng/ml) and oligonucleotides (2006: CpG phosphorothioate; 2117 methylated 2006; 2 μg/ml), CD83 and CD86 expression on dendritic cells is determined in flow cytometry. Values (%) represent the percentage of CD83 positive (mature) cells of all viable cells. Results are representative for four independent experiments.

Mature human DC express the specific DC marker CD83, while immature DC do not. Mature DC effectively present antigen and maintain their stimulatory capacity while migrating from peripheral tissues to lymph nodes. Maturation of DC is thought to be essential if these cells are intended to be used for therapeutic strategies where they would be activated ex vivo, pulsed with antigens, and then reinfused into a patient. We looked at simultaneous expression of CD83 and the co-stimulatory molecule CD86 on viable DC (FIG. 9). Freshly isolated DC were incubated for 3 days with GMCSF, LPS or oligonucleotides. In the absence of either GMCSF or CpG, or with the methylated control oligonucleotide 2117 (2 μg/ml), survival of cells was poor. The remaining viable cells did not express CD83 (<2%) or CD86 (FIG. 9, right dot plot, middle row). Cells incubated with GMCSF showed low expression of CD86, and only 4.1% of the cells expressed CD83 (FIG. 9, left dot plot, lower row). If LPS (10 ng/ml) is present in addition to GMCSF, the percentage of CD83 positive cells is increased to 8.6% (FIG. 9, right dot plot, lower row). In contrast, the single addition of 2006 (2 μg/ml) renders 16% of the DC CD83 positive (FIG. 9, left dot plot, middle row). The combination of GMCSF and 2006 even enhances CD83 expression synergistically (37%) (FIG. 9, left dot plot, upper row). This induction of CD83 expression was CpG specific as shown by the control oligonucleotide 2117 in combination with GMCSF (9.7%) (FIG. 9, right dot plot, upper row). Independently of the percentage of CD83 positive cells, cells positive for CD83 also expressed higher levels of CD86. The results of FIG. 9 are representative of four independent experiments.

Example 6

Ultrastructural Changes of DC in Response to CpG

Results

Figure 10A:
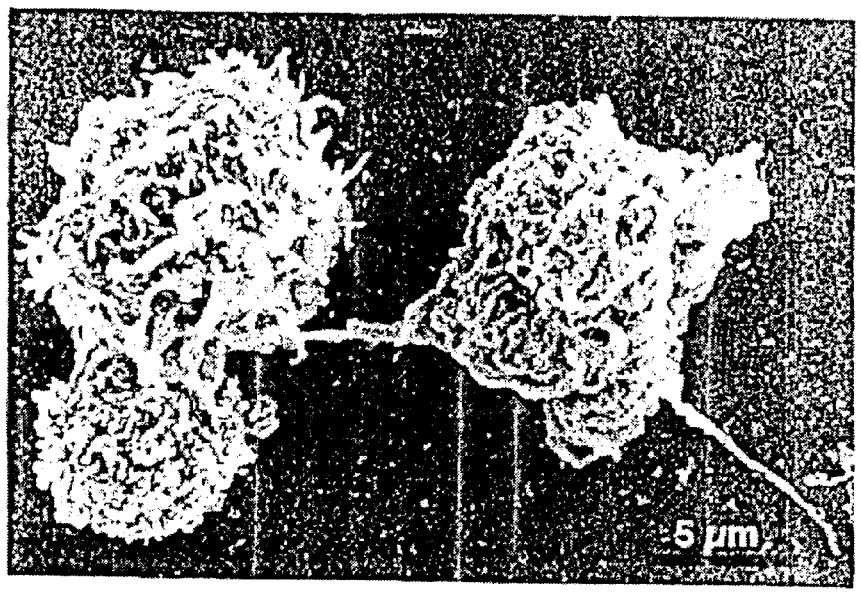
FIG. 10 are electron micrographs depicting CpG induction of morphologic changes in dendritic cells. Dendritic cells were incubated for 2 days in the presence of GMCSF (800 U/ml) and 2006 (2 μg/ml) (panel A), with 2006 (2 μg/ml) (panel B), with GMCSF (800 U/ml) (panel C), and with the control oligonucleotide 2117 (2 μg/ml) (panel D). Cells were fixed and processed for scanning electron microscopy according to standard procedures.
Figure 10B:
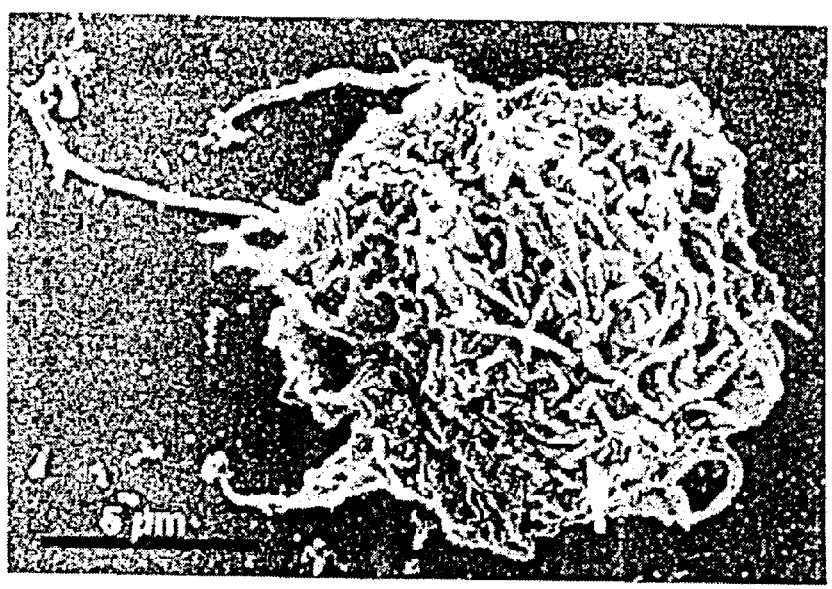
Figure 10C:
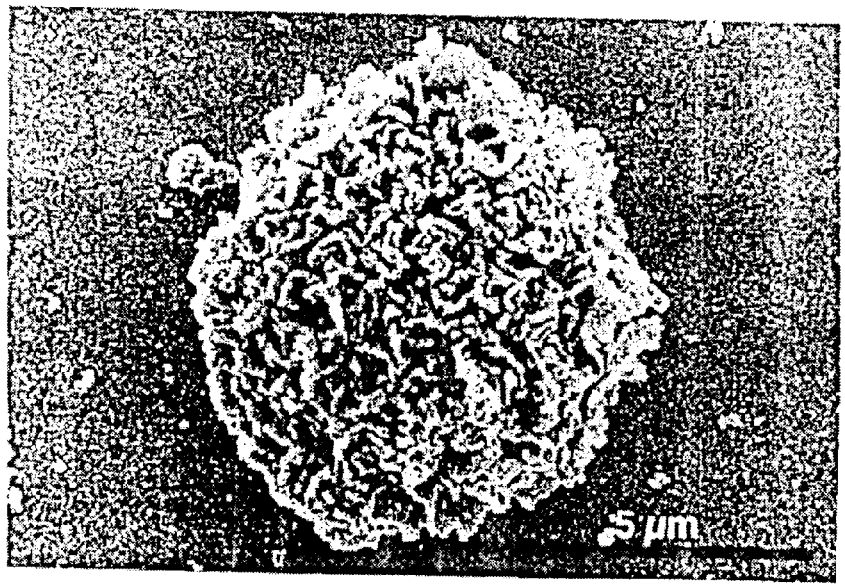
Figure 10D:
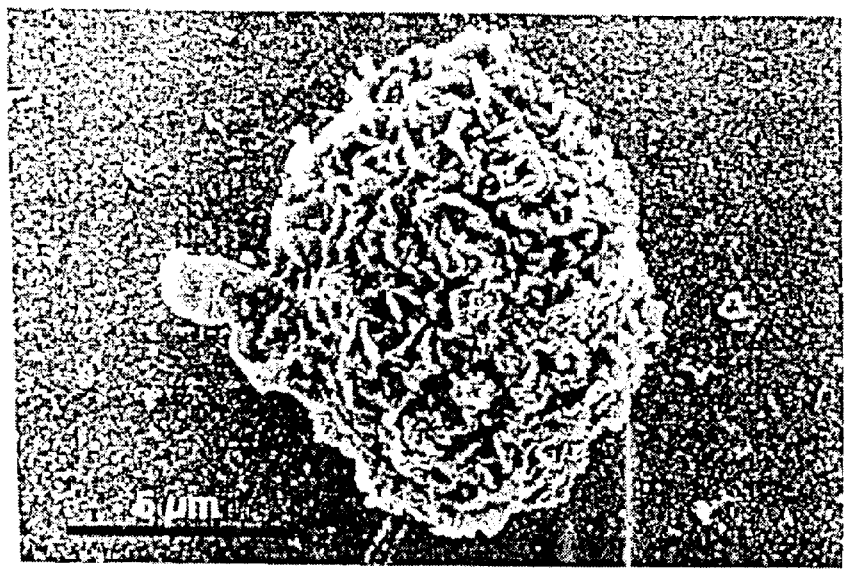
Figure 11A:
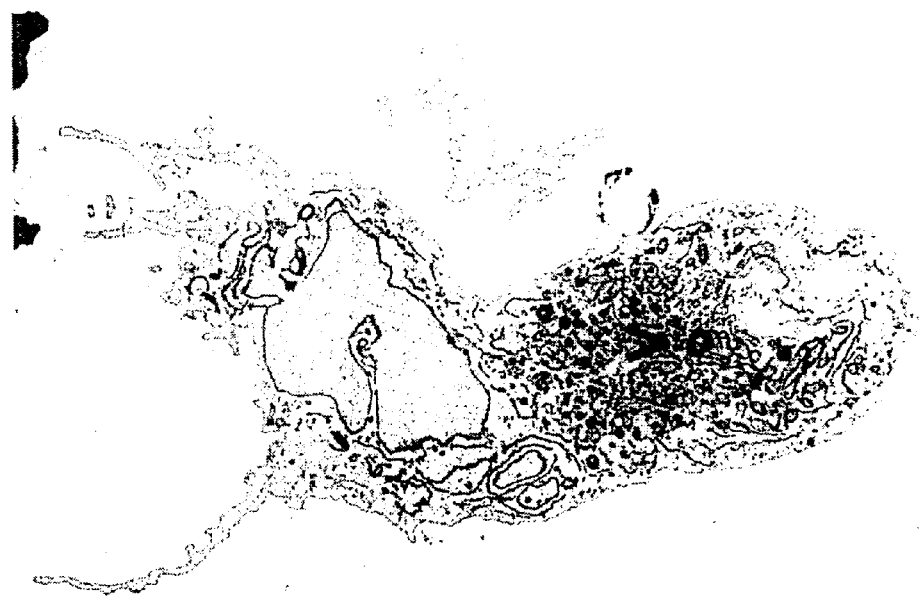
FIG. 11 are electron micrographs depicting Ultrastructural differences due to CpG Dendritic cells were incubated for 2 days in the presence of GMCSF (800 U/ml) and 2006 (2 μg/ml) (panel A) or with GMCSF (800 U/ml) (panel B) and transmission electron microscopy was performed. In the presence of CpG (panel A) multilamellar bodies (>) and multivesicular structures can be seen.
Figure 11B:
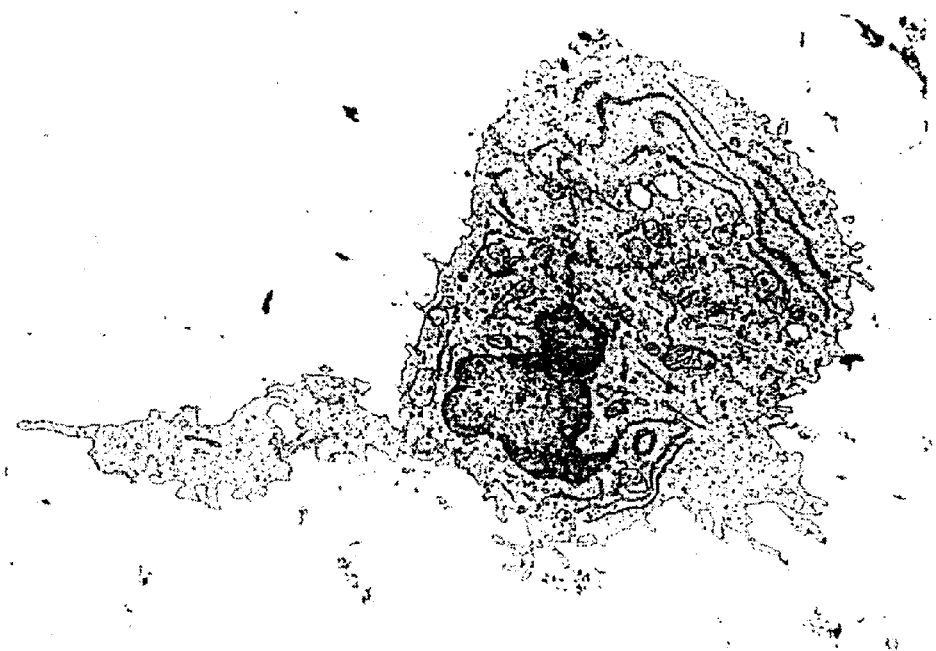
Figure 12A:
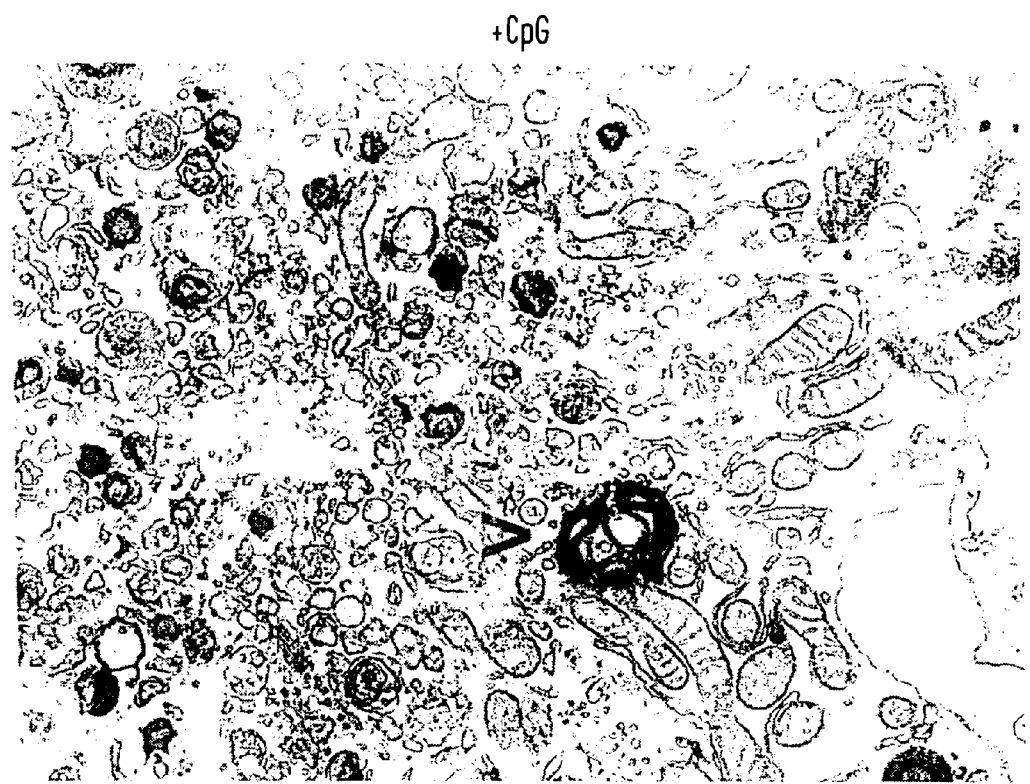
FIG. 12 are electron micrographs depicting High magnification of CpG-characteristic ultrastructural differences. Dendritic cells incubated with GMCSF (800 U/ml) and 2006 (2 μg/ml) were examined by transmission electron microscopy. Arrows point to characteristic multilarnellar bodies (>) and to multivesicular structures (>>).
Figure 12B:
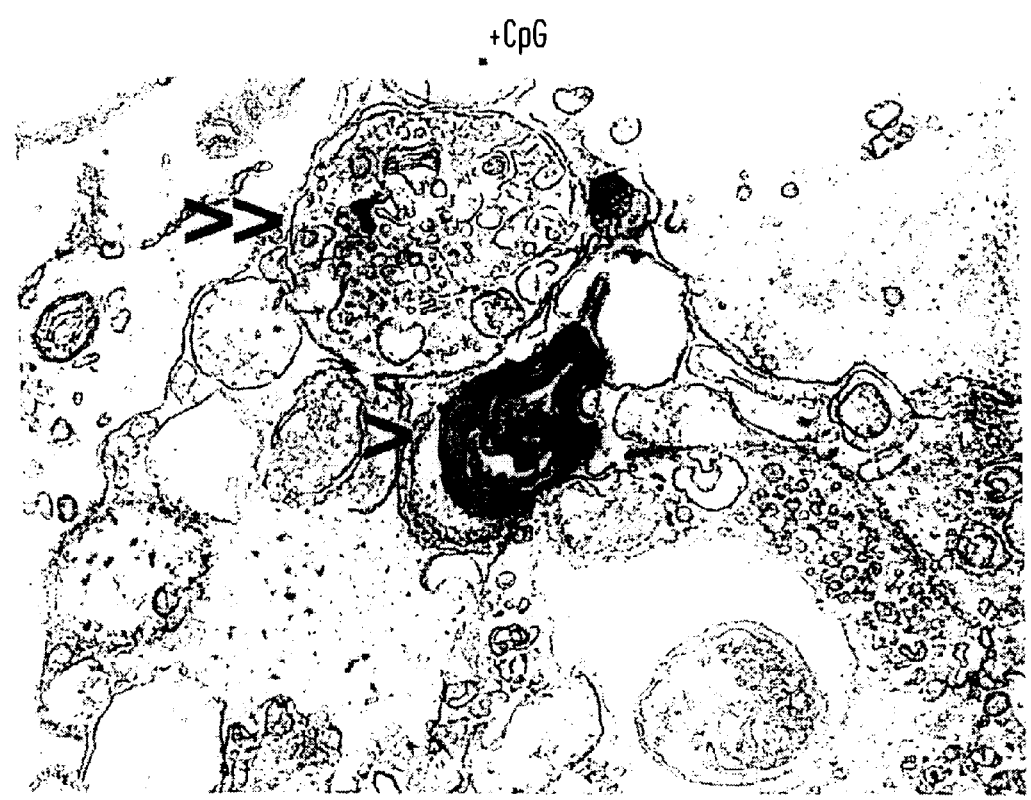

We examined DC by electron microscopy to detect ultrastructural differences due to CpG. In scanning electron microscopy (FIG. 10), DC cultivated with either GMCSF and CpG (FIG. 10 A) or with CpG alone (FIG. 10B) displayed a more irregular shape, longer veil processes and sheet-like projections, and more intercellular contacts than cells cultivated with GMCSF alone (FIG. 10C) or in combination with the non-CpG control oligonucleotide (FIG. 10D). Transmission electron microscopic imaging revealed striking differences between DC generated with GMCSF combined with CpG (FIG. 11A) and GMCSF alone (FIG. 11B). DC generated in the presence of CpG showed multi-lamellar intracytoplasmic bodies of high density (FIG. 11A, FIG. 12, indicated by >), which are absent without CpG (FIG. 11B). In addition, CpG-generated DC showed prominent multivesicular bodies (FIG. 11A, FIG. 12, indicated by >>), and a less heterochromatin in the nucleus. The functional significance of these ultrastructural differences is unclear.

Statistical Analysis

Data were expressed as means +/−SEM. Statistical significance of differences was determined by the unpaired two-tailed Student's t-test. Differences were considered statistically significant for p<0.05. Statistical analyses were performed by using StatView 4.51 software (Abacus Concepts Inc., Calabasas, Calif.).

TABLE 1

| ODN | | Sequence (5' to 3')↑ |
|---|---|---|
| 1 | (SEQ ID NO:1) | GCTAGACGTTAGCGT |
| 1a | (SEQ ID NO:2) | ......T........._._. |
| 1b | (SEQ ID NO:3) | ......Z........._._. |
| 1c | (SEQ ID NO:4) | ........._._....Z.. |
| 1d | (SEQ ID NO:5) | ..AT..._._..GAGC. |
| 2 | (SEQ ID NO:6) | ATGGAAGGTCCAGCGTTCTC |
| 2a | (SEQ ID NO:7) | ..C...CTC..G..._._...... |
| 2b | (SEQ ID NO:8) | ..Z..CTC.ZG...Z...... |
| 2c | (SEQ ID NO:9) | ..Z..CTC..G..._._...... |
| 2d | (SEQ ID NO:10) | ..C...CTC..G..._._...Z.. |
| 2e | (SEQ ID NO:11) | ............A..._._...... |
| 3D | (SEQ ID NO:12) | GAGAACGCTGGACCTTCCAT |
| 3Da | (SEQ ID NO:13) | ........_._..C........ |
| 3Db | (SEQ ID NO:14) | ........_._..C......G.. |
| 3Dc | (SEQ ID NO:15) | ...C.A.............. |
| 3Dd | (SEQ ID NO:16) | .....Z............... |
| 3De | (SEQ ID NO:17) | ........_._......Z...... |
| 3Df | (SEQ ID NO:18) | ......_._A............ |
| 3Dg | (SEQ ID NO:19) | ........_._..CC.G.ACTG.. |
| 3M | (SEQ ID NO:20) | TCCATGTCGGTCCTGATGCT |
| 3Ma | (SEQ ID NO:21) | ......CT............ |
| 3Mb | (SEQ ID NO:22) | ......Z............. |
| 3Mc | (SEQ ID NO:23) | ........._._.Z......... |
| 3Md | (SEQ ID NO:24) | ......A..T........... |
| 3Me | (SEQ ID NO:25) | ........._._......C...A. |
| 4 | (SEQ ID NO:26) | TCAACGTT |
| 4a | (SEQ ID NO:27) | ....GC.. |
| 4b | (SEQ ID NO:28) | ...GCGC. |
| 4c | (SEQ ID NO:29) | ...TCGA. |
| 4d | (SEQ ID NO:30) | ..TT..AA |
| 4e | (SEQ ID NO:31) | -..._._.. |
| 4f | (SEQ ID NO:32) | C..._._.. |
| 4g | (SEQ ID NO:33) | --..._._.CT |
| 4h | (SEQ ID NO:34) | ......_._.C |

TABLE 2

| 5a | SEQ.ID.No:3 | ATGGACTCTCCAGCGTTCTC | |
|---|---|---|---|
| 5b | SEQ.ID.No:36 | .....AGG....A..._._...... | |
| 5c | SEQ.ID.No:37 | ..C......G..._._...... | |
| 5d | SEQ.ID.No:38 | ....AGG..C..T...... | ≦10 |
| 5e | SEQ.ID.No:40 | ..C......G..Z...... | |
| 5f | SEQ.ID.No:39 | ..Z......ZG..Z...... | ≦10 |
| 5g | SEQ.ID.No:41 | ..C......G......Z.. | |
| | 5'GCATGACGTTGAGCT3' | (SEQ.ID.No:42) | |
| | 5'GCTAGATGTTAGCGT3' | (SEQ.ID.No:43) | |

TABLE 3

| 512 | TCCATGTCGGTCCTGATGCT |
|---|---|
| SEQ ID NO:44 | |
| 1637 | ......C...._._............ |
| SEQ ID NO:45 | |
| 1615 | ......G...._._............ |
| SEQ ID NO:46 | |
| 1614 | ......A...._._............ |
| SEQ ID NO:47 | |
| 1636 | ........_._A.......... |
| SEQ ID NO:48 | |
| 1634 | ........_._C.......... |
| SEQ ID NO:49 | |
| 1619 | ........_._T.......... |
| SEQ ID NO:50 | |
| 1618 | ......A_._T.......... |
| SEQ ID NO:51 | |
| 1639 | .....AA_._T.......... |
| SEQ ID NO:52 | |
| 1707 | ......A_._TC.......... |
| SEQ ID NO:53 | |
| 1708 | .....CA_._TG.......... |
| SEQ ID NO:54 | |

TABLE 4

| 1585 | | |
|---|---|---|
| ggGGTCAACGTTGACgggg | | (SEQ ID No 55) |
| 1629 | | |
| ------gtc--------- | | (SEQ ID No 56) |
| 1613 | | |
| GCTAGACGTTAGTGT | | (SEQ ID No 57) |
| 1769 | | |
| -------Z------ | | (SEQ ID No 58) |
| 1619 | | |
| TCCATGTCGTTCCTGATGCT | | (SEQ ID No 59) |
| 1765 | | |
| -------Z---------- | | (SEQ ID No 60) |

TABLE 5

| ODN | Sequence (5'−3') | SEQ ID NO. |
|---|---|---|
| 1754 | ACCATGGACGATCTGTTTCCCCTC | 61 |
| 1758 | TCTCCCAGCGTGCGCCAT | 62 |
| 1761 | TACCGCGTGCGACCCTCT | 63 |
| 1776 | ACCATGGACGAACTGTTTCCCCTC | 64 |
| 1777 | ACCATGGACGAGCTGTTTCCCCTC | 65 |
| 1778 | ACCATGGACGACCTGTTTCCCCTC | 66 |
| 1779 | ACCATGGACGTACTGTTTCCCCTC | 67 |
| 1780 | ACCATGGACGGTCTGTTTCCCCTC | 68 |
| 1781 | ACCATGGACGTTCTGTTTCCCCTC | 69 |
| 1823 | GCATGACGTTGAGCT | 70 |
| 1824 | CACGTTGAGGGCAT | 71 |
| 1825 | CTGCTGAGACTGGAG | 72 |
| 1828 | TCAGCGTGCGCC | 73 |
| 1829 | ATGACGTTCCTGACGTT | 74 |
| 1830[2] | RANDOM SEQUENCE | 75 |
| 1834 | TCTCCCAGCGGGCGCAT | 76 |
| 1836 | TCTCCCAGCGCGCGCCAT | 77 |
| 1840 | TCCATGTCGTTCCTGTCGTT | 78 |
| 1841 | TCCATAGCGTTCCTAGCGTT | 79 |
| 1842 | TCGTCGCTGTCTCCGCTTCTT | 80 |
| 1851 | TCCTGACGTTCCTGACGTT | 81 |

TABLE 6

| ODN[1] | sequence (5'−3') | |
|---|---|---|
| 1840 | TCCATGTCGTTCCTGTCGTT | 82 |
| 1960 | TCCTGTCGTTCCTGTCGTT | 83 |
| 1961 | TCCATGTCGTTTTTGTCGTT | 84 |
| 1962 | TCCTGTCGTTCCTTGTCGTT | 85 |

TABLE 6-continued

| ODN[1] | sequence (5'—3') | |
|---|---|---|
| 1963 | TCCTTGTCGTTCCTGTCGTT | 86 |
| 1965 | TCCTGTCGTTTTTGTCGTT | 87 |
| 1966 | TCGTCGCTGTCTCCGCTTCTT | 88 |
| 1967 | TCGTCGCTGTCTGCCCTTCTT | 89 |
| 1968 | TCGTCGCTGTTGTCGTTTCTT | 90 |
| 1979[2] | TCCATGTZGTTCCTGTZGTT | 91 |
| 1982 | TCCAGGACTTCTCTCAGGTT | 92 |
| 1990 | TCCATGCGTGCGTGCGTTTT | 93 |
| 1991 | TCCATGCGTTGCGTTGCGTT | 94 |
| 2002 | TCCACGACGTTTTCGACGTT | 95 |
| 2005 | TCGTCGTTGTCGTTGTCGTT | 96 |
| 2006 | TCGTCGTTTTGTCGTTTTGTCGTT | 97 |
| 2007 | TCGTCGTTGTCGTTTTGTCGTT | 98 |
| 2008 | GCGTGCGTTGTCGTTGTCGTT | 99 |
| 2010 | GCGGCGGGCGGCGCGCGCCC | 100 |
| 2012 | TGTCGTTTGTCGTTTGTCGTT | 101 |
| 2013 | TGTCGTTGTCGTTGTCGTTGTCGTT | 102 |
| 2014 | TGTCGTTGTCGTTGTCGTT | 103 |
| 2015 | TCGTCGTCGTCGTT | 104 |
| 2016 | TGTCGTTGTCGTT | 105 |
| 1841 | TCCATAGCGTTCCTAGCGTT | 106 |

TABLE 7

| ODN[1] | sequence (5'—3') | |
|---|---|---|
| 1962 | TCCTGTCGTTCCTTGTCGTT | 107 |
| 1965 | TCCTGTCGTTTTTGTCGTT | 108 |
| 1967 | TCGTCGCTGTCTGCCCTTCTT | 109 |

TABLE 7-continued

| ODN[1] | sequence (5'—3') | |
|---|---|---|
| 1968 | TCGTCGCTGTTGTCGTTTCTT | 110 |
| 2005 | TCGTCGTTGTCGTTGTCGTT | 111 |
| 2006 | TCGTCGTTTTGTCGTTTTGTCGTT | 112 |
| 2014 | TGTCGTTGTCGTTGTCGTT | 113 |
| 2015 | TCGTCGTCGTCGTT | 114 |
| 2016 | TGTCGTTGTCGTT | 115 |
| 1668 | TCCATGACGTTCCTGATGCT | (SEQ.ID.NO 116) |
| 1758 | TCTCCCAGCGTGCGCCAT | (SEQ.ID.NO 117) |

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

All references, patents and patent publications that are recited in this application are incorporated in their entirety herein by reference.

We claim:

1. A method for activating a dendritic cell, comprising: contacting a dendritic cell with an isolated nucleic acid containing at least one unmethylated CpG dinucleotide wherein the nucleic acid is from about 8–80 bases in length in an amount effective to activate a dendritic cell, wherein the method is performed ex vivo.

2. A method for activating a dendritic cell, comprising: contacting a dendritic cell with an isolated nucleic acid containing at least one unmethylated CpG dinucleotide wherein the nucleic acid is from about 8–80 bases in length in an amount effective to activate the dendritic cell, wherein the dendritic cell is an isolated dendritic cell.

3. The method of claim 1, wherein the isolated nucleic acid has a formula:

$$5'N_1X_1CGX_2N_23'$$

wherein at least one nucleotide separates consecutive CpGs; $X_1$ is adenine, guanine, or thymine; $X_2$ is cytosine, adenine, or thymine; N is any nucleotide and $N_1+N_2$ is from about 0–25 nucleotides.

4. The method of claim 2, wherein the method is performed ex vivo.

5. The method of claim 4, further comprising contacting the dendritic cell with an antigen prior to the isolated nucleic acid.

6. A method for activating a dendritic cell, comprising: contacting a dendritic cell with an isolated nucleic acid containing at least one unmethylated CpG dinucleotide wherein the nucleic acid is from about 8–80 bases in length in an amount effective to activate the dendritic cell, wherein at least one nucleotide of the isolated nucleic acid has a phosphate backbone modification where in the method is peformed ex vivo.

7. The method of claim 6, wherein the phosphate backbone modification is a phosphorothioate or phosphorodithioate modification.

8. The method of claim 7, wherein the phosphate backbone modification occures at the 5' end of the nucleic acid.

9. The method of claim 8, wherein the nucleic acid backbone includes the phosphate backbone modification at the 5' internucleotide linkages.

10. The method of claim 7, wherein the nucleic acid backbone includes the phosphate backbone modification at the 3' internucleotide linkages.

11. The method of claim 10, wherein the phosphate backbone modification occurs at the last five internucleotide linkages of the 3' end of the nucleic acid.

12. The method of claim 1, wherein the isolated nucleic acid has a formula:

$$5'N_1X_1X_2CGX_3X_4N_23'$$

wherein at least one nucleotide separates consecutive CpGs; $X_1X_2$ is selected from the group consisting of TpT, CpT, TpC, and ApT; $X_3X_4$ is selected from the group consisting of GpT, GpA, ApA and ApT; N is any nucleotide and $N_1+N_2$ is from about 0–25 nucleotides.

13. A method for activating a dendritic cell, comprising:

contacting a dendritic cell with an isolated nucleic acid containing at least one unmethylated CpG dinucleotide in an amount effective to activate the dendritic cell, wherein the isolated nucleic acid is selected from the group consisting of SEQ ID Nos. 84 and 85.

14. A method for cancer immunotherapy, comprising:

administering an activated dendritic cell that expresses a specific cancer antigen to a subject having a cancer including the cancer antigen, wherein the activated dendritic cell is prepared by contacting a dendritic cell with an isolated nucleic acid containing at least one unmethylated CpG dinucleotide wherein the nucleic acid is from about 8–80 bases in length in an amount effective to activate the dendritic cell.

15. A method for treating an infectious disease, comprising:

administering an activated dendritic cell that expresses a specific microbial antigen to a subject having an infection with a microorganism including the microbial antigen, wherein the activated dendritic cell is prepared by contacting a dendritic cell with an isolated nucleic acid containing at least one unmethylated CpG dinucleotide wherein the nucleic acid is from about 8–80 bases in length in an amount effective to activate the dendritic cell.

16. A method for treating an allergy, comprising:

administering an activated dendritic cell that expresses a specific allergy causing antigen to a subject having an allergic reaction to the allergy causing antigen, wherein the activated dendritic cell is prepared by contacting a dendritic cell with an isolated nucleic acid containing at least one unmethylated CpG dinucleotide wherein the nucleic is from about 8–80 bases in length in an amount effective to activate the dendritic cell.

17. A method for generating a high yield of dendritic cells, comprising:

administering an isolated nucleic acid containing at least one unmethylated CpG dinucleotide wherein the nucleic acid is from about 8–80 bases in length in an amount effective for activating dendritic cells to a subject;

allowing the isolated nucleic acid to activate dendritic cells of the subject; and isolating dendritic cells from the subject.

18. A method for causing maturation of a dendritic cell, comprising contacting a dendritic cell with an isolated nucleic acid containing at least one unmethylated CpG dinucleotide wherein the nucleic acid is from about 8–80 bases in length in an amount effective to cause maturation of the dendritic cell.

19. A method for activating a dendritic cell, comprising:

contacting a dendritic cell with an effective amount to activate a dendritic cell of an isolated nucleic acid containing at least one unmethylated CpG dinucleotide and an antigen.

20. The method of claim 19, wherein the dendritic cell is contacted with the antigen within 48 hours of contacting the dendritic cell with the isolated nucleic acid.

21. The method of claim 19, wherein the dendritic cell is contacted with the antigen within 24 hours of contacting the dendritic cell with the isolated nucleic acid.

* * * * *

SEQUENCE LISTING

```
<160> NUMBER OF SEQ ID NOS: 99

<210> SEQ ID NO 1
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 1
gctagacgtt agcgt                                                      15

<210> SEQ ID NO 2
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 2
gctagatgtt agcgt                                                      15

<210> SEQ ID NO 3
<211> LENGTH: 15
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: (7)...(7)
<223> OTHER INFORMATION: m5c
```

```
<400> SEQUENCE: 3
gctagacgtt agcgt                                            15

<210> SEQ ID NO 4
<211> LENGTH: 15
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: (13)...(13)
<223> OTHER INFORMATION: m5c

<400> SEQUENCE: 4
gctagacgtt agcgt                                            15

<210> SEQ ID NO 5
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 5
gcatgacgtt gagct                                            15

<210> SEQ ID NO 6
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 6
atggaaggtc cagcgttctc                                       20

<210> SEQ ID NO 7
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 7
atcgactctc gagcgttctc                                       20

<210> SEQ ID NO 8
<211> LENGTH: 20
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: (3)...(3)
<223> OTHER INFORMATION: m5c
<220> FEATURE:
<221> NAME/KEY: modified_base
<222> LOCATION: (10)...(10)
<223> OTHER INFORMATION: m5c
<220> FEATURE:
<221> NAME/KEY: modified_base
<222> LOCATION: (14)...(14)
<223> OTHER INFORMATION: m5c

<400> SEQUENCE: 8
atcgactctc gagcgttctc                                       20
```

```
<210> SEQ ID NO 9
<211> LENGTH: 20
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: (3)...(3)
<223> OTHER INFORMATION: m5c

<400> SEQUENCE: 9
atcgactctc gagcgttctc                                          20

<210> SEQ ID NO 10
<211> LENGTH: 20
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: (18)...(18)
<223> OTHER INFORMATION: m5c

<400> SEQUENCE: 10
atcgactctc gagcgttctc                                          20

<210> SEQ ID NO 11
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 11
atggaaggtc caacgttctc                                          20

<210> SEQ ID NO 12
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 12
gagaacgctg gaccttccat                                          20

<210> SEQ ID NO 13
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 13
gagaacgctc gaccttccat                                          20

<210> SEQ ID NO 14
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 14
```
gagaacgctc gaccttcgat                                          20

<210> SEQ ID NO 15
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 15
gagcaagctg gaccttccat                                          20

<210> SEQ ID NO 16
<211> LENGTH: 20
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: (6)...(6)
<223> OTHER INFORMATION: m5c

<400> SEQUENCE: 16
gagaacgctg gaccttccat                                          20

<210> SEQ ID NO 17
<211> LENGTH: 20
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: (14)...(14)
<223> OTHER INFORMATION: m5c

<400> SEQUENCE: 17
gagaacgctg gaccttccat                                          20

<210> SEQ ID NO 18
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 18
gagaacgatg gaccttccat                                          20

<210> SEQ ID NO 19
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 19
gagaacgctc cagcactgat                                          20

<210> SEQ ID NO 20
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 20

```
tccatgtcgg tcctgatgct                                               20

<210> SEQ ID NO 21
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 21
tccatgctgg tcctgatgct                                               20

<210> SEQ ID NO 22
<211> LENGTH: 20
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: (8)...(8)
<223> OTHER INFORMATION: m5c

<400> SEQUENCE: 22
tccatgtcgg tcctgatgct                                               20

<210> SEQ ID NO 23
<211> LENGTH: 20
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: (12)...(12)
<223> OTHER INFORMATION: m5c

<400> SEQUENCE: 23
tccatgtcgg tcctgatgct                                               20

<210> SEQ ID NO 24
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 24
tccatgacgt tcctgatgct                                               20

<210> SEQ ID NO 25
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 25
tccatgtcgg tcctgctgat                                               20

<210> SEQ ID NO 26
<211> LENGTH: 8
<212> TYPE: DNA
<213> ORGANISM: Artificial Sequence
<220> FEATURE:
<223> OTHER INFORMATION: synthetic oligonucleotide
```

```
<400> SEQUENCE: 26 tcaacgtt                                                                          8

<210> SEQ ID NO 27
<211> LENGTH: 8
<212> TYPE: DNA
<213> ORGANISM: Artificial Sequence
<220> FEATURE:
<223> OTHER INFORMATION: synthetic oligonucleotide

<400> SEQUENCE: 27 tcaagctt                                                                          8

<210> SEQ ID NO 28
<211> LENGTH: 8
<212> TYPE: DNA
<213> ORGANISM: Artificial Sequence
<220> FEATURE:
<223> OTHER INFORMATION: synthetic oligonucleotide

<400> SEQUENCE: 28 tcagcgct                                                                          8

<210> SEQ ID NO 29
<211> LENGTH: 8
<212> TYPE: DNA
<213> ORGANISM: Artificial Sequence
<220> FEATURE:
<223> OTHER INFORMATION: synthetic oligonucleotide

<400> SEQUENCE: 29 tcatcgat                                                                          8

<210> SEQ ID NO 30
<211> LENGTH: 8
<212> TYPE: DNA
<213> ORGANISM: Artificial Sequence
<220> FEATURE:
<223> OTHER INFORMATION: synthetic oligonucleotide

<400> SEQUENCE: 30 tcttcgaa                                                                          8

<210> SEQ ID NO 31
<211> LENGTH: 7
<212> TYPE: DNA
<213> ORGANISM: Artificial Sequence
<220> FEATURE:
<223> OTHER INFORMATION: synthetic oligonucleotide

<400> SEQUENCE: 31 caacgtt                                                                           7

<210> SEQ ID NO 32
<211> LENGTH: 8
<212> TYPE: DNA
<213> ORGANISM: Artificial Sequence
<220> FEATURE:
<223> OTHER INFORMATION: synthetic oligonucleotide

<400> SEQUENCE: 32 ccaacgtt                                                                          8

<210> SEQ ID NO 33
<211> LENGTH: 8
```

```
<212> TYPE: DNA
<213> ORGANISM: Artificial Sequence
<220> FEATURE:
<223> OTHER INFORMATION: synthetic oligonucleotide

<400> SEQUENCE: 33 aacgttct                                                                8

<210> SEQ ID NO 34
<211> LENGTH: 8
<212> TYPE: DNA
<213> ORGANISM: Artificial Sequence
<220> FEATURE:
<223> OTHER INFORMATION: synthetic oligonucleotide

<400> SEQUENCE: 34 tcaacgtc                                                                8

<210> SEQ ID NO 35
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 35
atggactctc cagcgttctc                                                  20

<210> SEQ ID NO 36
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 36
atggaggctc catcgttctc                                                  20

<210> SEQ ID NO 37
<211> LENGTH: 20
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: (14)...(14)
<223> OTHER INFORMATION: m5c

<400> SEQUENCE: 37
atcgactctc gagcgttctc                                                  20

<210> SEQ ID NO 38
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 38
tccatgccgg tcctgatgct                                                  20

<210> SEQ ID NO 39
<211> LENGTH: 20
<212> TYPE: DNA
<213> ORGANISM: Artificial Sequence
<220> FEATURE:
```

-continued

<223> OTHER INFORMATION: synthetic oligonucleotide

<400> SEQUENCE: 39
tccatggcgg tcctgatgct                                               20

<210> SEQ ID NO 40
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 40
tccatgacgg tcctgatgct                                               20

<210> SEQ ID NO 41
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 41
tccatgtcga tcctgatgct                                               20

<210> SEQ ID NO 42
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 42
tccatgtcgc tcctgatgct                                               20

<210> SEQ ID NO 43
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 43
tccatgtcgt tcctgatgct                                               20

<210> SEQ ID NO 44
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 44
tccataacgt tcctgatgct                                               20

<210> SEQ ID NO 45
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 45
tccatgacgt ccctgatgct                                               20

```
<210> SEQ ID NO 46
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 46
tccatcacgt gcctgatgct                                                 20

<210> SEQ ID NO 47
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 47
ggggtcaacg ttgaggggggg                                                20

<210> SEQ ID NO 48
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 48
ggggtcagtc ttgacgggg                                                  19

<210> SEQ ID NO 49
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 49
gctagacgtt agtgt                                                      15

<210> SEQ ID NO 50
<211> LENGTH: 15
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: (8)...(8)
<223> OTHER INFORMATION: m5c

<400> SEQUENCE: 50 gctagaccatt agtgt                                                     15

<210> SEQ ID NO 51
<211> LENGTH: 20
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: (8)...(8)
<223> OTHER INFORMATION: m5c

<400> SEQUENCE: 51
tccatgtcgt tcctgatgct                                                 20
```

```
<210> SEQ ID NO 52
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 52
accatggacg atctgtttcc cctc                                          24

<210> SEQ ID NO 53
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 53
tctcccagcg tgcgccat                                                 18

<210> SEQ ID NO 54
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 54
taccgcgtgc gaccctct                                                 18

<210> SEQ ID NO 55
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 55
accatggacg aactgtttcc cctc                                          24

<210> SEQ ID NO 56
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 56
accatggacg agctgtttcc cctc                                          24

<210> SEQ ID NO 57
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 57
accatggacg acctgtttcc cctc                                          24

<210> SEQ ID NO 58
<211> LENGTH: 24
<212> TYPE: DNA
<213> ORGANISM: Artificial Sequence
<220> FEATURE:
<223> OTHER INFORMATION: synthetic oligonucleotide
```

<400> SEQUENCE: 58
accatggacg tactgtttcc cctc                24

<210> SEQ ID NO 59
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 59
accatggacg gtctgtttcc cctc                24

<210> SEQ ID NO 60
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 60
accatggacg ttctgtttcc cctc                24

<210> SEQ ID NO 61
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 61
cacgttgagg ggcat                15

<210> SEQ ID NO 62
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 62
ctgctgagac tggag                15

<210> SEQ ID NO 63
<211> LENGTH: 12
<212> TYPE: DNA
<213> ORGANISM: Artificial Sequence
<220> FEATURE:
<223> OTHER INFORMATION: synthetic oligonucleotide

<400> SEQUENCE: 63
tcagcgtgcg cc                12

<210> SEQ ID NO 64
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 64
atgacgttcc tgacgtt                17

<210> SEQ ID NO 65

```
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 65
tctcccagcg ggcgcat                                                    17

<210> SEQ ID NO 66
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 66
tctcccagcg cgcgccat                                                   18

<210> SEQ ID NO 67
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 67
tccatgtcgt tcctgtcgtt                                                 20

<210> SEQ ID NO 68
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 68
tccatagcgt tcctagcgtt                                                 20

<210> SEQ ID NO 69
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 69
tcgtcgctgt ctccgcttct t                                               21

<210> SEQ ID NO 70
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 70
tcctgacgtt cctgacgtt                                                  19

<210> SEQ ID NO 71
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 71
```

-continued tcctgtcgtt cctgtcgtt                                            19

<210> SEQ ID NO 72
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 72
tccatgtcgt ttttggcgtt                                           20

<210> SEQ ID NO 73
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 73
tcctgtcgtt ccttgtcgtt                                           20

<210> SEQ ID NO 74
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 74
tccttgtcgt tcctgtcgtt                                           20

<210> SEQ ID NO 75
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 75
tcctgtcgtt ttttgtcgtt                                           20

<210> SEQ ID NO 76
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 76
tcgtcgctgt ctgcccttct t                                         21

<210> SEQ ID NO 77
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 77
tcgtcgctgt tgtcgtttct t                                         21

<210> SEQ ID NO 78
<211> LENGTH: 20
<212> TYPE: DNA

```
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: (8)...(8)
<223> OTHER INFORMATION: m5c
<220> FEATURE:
<221> NAME/KEY: modified_base
<222> LOCATION: (17)...(17)
<223> OTHER INFORMATION: m5c

<400> SEQUENCE: 78
tccatgtcgt tcctgtcgtt                                              20

<210> SEQ ID NO 79
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 79
tccaggactt ctctcaggtt                                              20

<210> SEQ ID NO 80
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 80
tccatgcgtg cgtgcgtttt                                              20

<210> SEQ ID NO 81
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 81
tccatgcgtt gcgttgcgtt                                              20

<210> SEQ ID NO 82
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 82
tccacgacgt tttcgacgtt                                              20

<210> SEQ ID NO 83
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 83
tcgtcgttgt cgttgtcgtt                                              20

<210> SEQ ID NO 84
<211> LENGTH: 24
```

```
<212> TYPE: DNA
<213> ORGANISM: Artificial Sequence
<220> FEATURE:
<223> OTHER INFORMATION: synthetic oligonucleotide

<400> SEQUENCE: 84
tcgtcgtttt gtcgttttgt cgtt                                    24

<210> SEQ ID NO 85
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 85
tcgtcgttgt cgttttgtcg tt                                      22

<210> SEQ ID NO 86
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 86
gcgtgcgttg tcgttgtcgt t                                       21

<210> SEQ ID NO 87
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 87
gcggcgggcg gcgcgcgccc                                         20

<210> SEQ ID NO 88
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 88
tgtcgtttgt cgtttgtcgt t                                       21

<210> SEQ ID NO 89
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 89
tgtcgttgtc gttgtcgttg tcgtt                                   25

<210> SEQ ID NO 90
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 90
```
tgtcgttgtc gttgtcgtt                                                19

<210> SEQ ID NO 91
<211> LENGTH: 14
<212> TYPE: DNA
<213> ORGANISM: Artificial Sequence
<220> FEATURE:
<223> OTHER INFORMATION: synthetic oligonucleotide

<400> SEQUENCE: 91
tcgtcgtcgt cgtt                                                     14

<210> SEQ ID NO 92
<211> LENGTH: 13
<212> TYPE: DNA
<213> ORGANISM: Artificial Sequence
<220> FEATURE:
<223> OTHER INFORMATION: synthetic oligonucleotide

<400> SEQUENCE: 92
tgtcgttgtc gtt                                                      13

<210> SEQ ID NO 93
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 93
ctggtctttc tggttttttt ctgg                                          24

<210> SEQ ID NO 94
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 94
tcgtcgttcc cccccccccc                                               20

<210> SEQ ID NO 95
<211> LENGTH: 24
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: (2)...(2)
<223> OTHER INFORMATION: m5c
<220> FEATURE:
<221> NAME/KEY: modified_base
<222> LOCATION: (5)...(5)
<223> OTHER INFORMATION: m5c
<220> FEATURE:
<221> NAME/KEY: modified_base
<222> LOCATION: (13)...(13)
<223> OTHER INFORMATION: m5c
<220> FEATURE:
<221> NAME/KEY: modified_base
<222> LOCATION: (21)...(21)
<223> OTHER INFORMATION: m5c

<400> SEQUENCE: 95
tcgtcgtttt gtcgttttgt cgtt                                          24

```
<210> SEQ ID NO 96
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 96
tgctgcttcc cccccccccc                                          20

<210> SEQ ID NO 97
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 97
tccatgacgt tcctgacgtt                                          20

<210> SEQ ID NO 98
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 98
tccatgagct tcctgagtct                                          20

<210> SEQ ID NO 99
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 99
aaaatcaacg ttgaaaaaaa                                          20
```